United States Patent
Nishida et al.

(10) Patent No.: US 8,895,588 B2
(45) Date of Patent: Nov. 25, 2014

(54) PYRAZOLE COMPOUND

(75) Inventors: Haruyuki Nishida, Kanagawa (JP);
Ikuo Fujimori, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 247 days.

(21) Appl. No.: 13/260,507

(22) PCT Filed: Mar. 25, 2010

(86) PCT No.: PCT/JP2010/055257
§ 371 (c)(1),
(2), (4) Date: Dec. 27, 2011

(87) PCT Pub. No.: WO2010/110378
PCT Pub. Date: Sep. 30, 2010

(65) Prior Publication Data
US 2012/0095057 A1    Apr. 19, 2012

(30) Foreign Application Priority Data

Mar. 26, 2009   (JP) .................. 2009-077078

(51) Int. Cl.
*A61K 31/4439* (2006.01)
*C07D 401/04* (2006.01)
(52) U.S. Cl.
CPC .................. *C07D 401/04* (2013.01)
USPC ....................... 514/341; 546/276.1
(58) Field of Classification Search
USPC ........................ 546/276.1; 514/341
See application file for complete search history.

(56) References Cited

U.S. PATENT DOCUMENTS

| | | | |
|---|---|---|---|
| 3,285,991 | A | 11/1966 | Sellers |
| 5,910,506 | A | 6/1999 | Sugimoto et al. |
| 7,994,205 | B2 | 8/2011 | Hasuoka et al. |
| 2004/0024014 | A1 | 2/2004 | Fang et al. |
| 2008/0139639 | A1 | 6/2008 | Kajino et al. |
| 2009/0286783 | A1 | 11/2009 | Ibrahim et al. |
| 2010/0210696 | A1 | 8/2010 | Nishida et al. |
| 2011/0124626 | A1 | 5/2011 | Pooni et al. |
| 2011/0288040 | A1 | 11/2011 | Hasuoka et al. |

FOREIGN PATENT DOCUMENTS

| | | | |
|---|---|---|---|
| EP | 0295049 | B1 | 12/1988 |
| EP | 2005957 | A1 | 12/2008 |
| JP | 09-048778 | A | 2/1997 |
| WO | WO-93/09100 | A1 | 5/1993 |
| WO | WO-97/17070 | A1 | 5/1997 |
| WO | WO-98/28269 | A1 | 7/1998 |
| WO | WO-99/42463 | A1 | 8/1999 |
| WO | WO-2004/103968 | A1 | 12/2004 |
| WO | WO-2005/009389 | A3 | 2/2005 |
| WO | WO-2006/036024 | A1 | 4/2006 |
| WO | WO-2007/026916 | A1 | 3/2007 |
| WO | WO-2007/114338 | A1 | 10/2007 |
| WO | WO-2008/108380 | A2 | 9/2008 |
| WO | WO-2009/041447 | A1 | 4/2009 |
| WO | WO-2009/041705 | A2 | 4/2009 |

OTHER PUBLICATIONS

Dorwald, Side Reactions in Organic Synthesis, 2005, Wiley: VCH Weinheim Preface, pp. 1-15 & Chapter 8, pp. 279-308.*
Halazy et al "Studies on the Antitumor Agent CC-1065", Tetrahedron Letters, 25 (14), pp. 1421-1424 (1984).
Artico et al. "Structure-Based Design, Synthesis, and Biological Evaluation of Novel Pyrrolyl Aryl Sulfones: HIV-1 Non-Nucleoside Reverse Transcriptase Inhibitors Active at Nanomolar Concentrations", J. Med. Chem., vol. 43, pp. 1886-1891 (2000).
maoclinic.com—Zollinger-Ellison Syndrome—2012.
Indigestion (dyspepsia) medicine.net—2012.
Stomache Cancer—mayoclinic.com—2012.
GastricMALTLymphoma-Lymphona Association2011.
Monkemuller, et al "Drug Treatment of Functional Dyspepsia", World J Gastroenterol, 12 (17), pp. 2694-2700 (2006).
Official Action issued on Jan. 29, 2013 in the corresponding Colombian Patent Application No. 11.14.548.
English Translation of the Official Action issued on Jan. 29, 2013 in the corresponding Colombian Patent Application No. 11.144.548.
International Search Report for International Application No. PCT/JP2010/055257, mailed on Jun. 1, 2010.
Email from Chilean Patent Attorney providing the Examiners Report No. 1 issued in corresponding Chilean Patent Application No. 2351-2011, dated Nov. 5, 2013.

* cited by examiner

*Primary Examiner* — Patricia L Morris
(74) *Attorney, Agent, or Firm* — Edwards Wildman Palmer LLP; George W. Neuner

(57) ABSTRACT

Provided is a compound having a superior acid secretion suppressive action, antiulcer activity and the like.
A compound represented by the formula

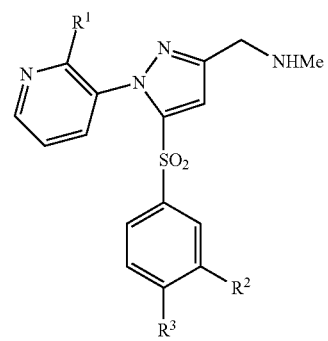

(1)

wherein $R^1$ is a substituent, $R^2$ is (i) a hydrogen atom, (ii) a $C_{1-6}$ alkyl group optionally having a halogen atom or (iii) a cyano group, $R^3$ is (i) a hydrogen atom, (ii) a halogen atom, (iii) a cyano group, (iv) a $C_{1-6}$ alkyl group optionally having a halogen atom or a $C_{1-6}$ alkoxy group optionally having a halogen atom, one of $R^2$ and $R^3$ is a hydrogen atom, and the other is a substituent other than a hydrogen atom, or a salt thereof.

4 Claims, No Drawings

PYRAZOLE COMPOUND

CROSS-REFERENCE TO RELATED APPLICATIONS

This application is the national phase application pursuant to 35 U.S.C. §371 of International Application No. PCT/JP2010/055257, filed Mar. 25, 2010, which claims the benefit of priority of Japanese Patent Application No. 077078/2009, filed Mar. 26, 2009. These applications are hereby incorporated herein by reference in their entireties.

TECHNICAL FIELD

The present invention relates to a pyrazole compound having an acid secretion suppressive activity.

BACKGROUND ART

Proton pump inhibitors represented by omeprazole, which suppress secretion of gastric acid for the treatment of peptic ulcer, reflux esophagitis and the like, have been widely used in clinical situations. However, the existing proton pump inhibitors are associated with problems in terms of effect and side effects. To be specific, since the existing proton pump inhibitors are unstable under acidic conditions, they are often formulated as enteric preparations, in which case several hours are required before onset of the effect, and about 5 days to exhibit maximum efficacy by consecutive administration. In addition, since the existing proton pump inhibitors show variation of treatment effects due to metabolic enzyme polymorphism and drug interaction with medicaments such as diazepam and the like, an improvement has been desired.

As compounds having a proton pump inhibitory action, patent document 1 describes a compound represented by the formula:

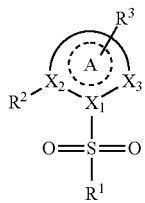

wherein
ring A is a saturated or unsaturated 5- or 6-membered ring group optionally containing, as a ring-constituting atom besides carbon atoms, 1 to 4 heteroatoms selected from a nitrogen atom, an oxygen atom and a sulfur atom, and the ring-constituting atoms $X_1$ and $X_2$ are each a carbon atom or a nitrogen atom, $R^1$ is an optionally substituted aryl group or an optionally substituted heteroaryl group, $R^2$ is an optionally substituted alkyl group, an optionally substituted aryl group or an optionally substituted heteroaryl group, and
$R^3$ is a substituent on the ring-constituting atom other than $X_1$, $X_2$ and $X_3$, which optionally has substituent(s) selected from a lower alkyl group, a halogen atom, a cyano group and oxo.

DOCUMENT LIST

Patent Document patent document 1: WO 2007/114338

SUMMARY OF THE INVENTION

A medicament that effectively suppresses gastric acid secretion like known proton pump inhibitors, which is improved in instability under acidic conditions, variability of effects due to metabolic enzyme polymorphism and drug interaction, which are problems of known proton pump inhibitors, is expected to show more superior treatment effect on peptic ulcer, reflux esophagitis and the like. It is therefore an object of the present invention to provide a compound having a superior acid secretion suppressive effect (particularly, proton pump inhibitory effect).

The present inventors have conducted various studies and found that a compound represented by the formula (I)

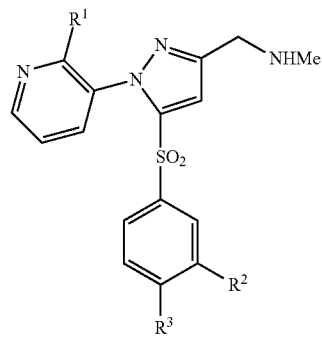

(I)

wherein $R^1$ is a substituent, $R^2$ is (i) a hydrogen atom, (ii) a $C_{1-6}$ alkyl group optionally having a halogen atom or (iii) a cyano group, $R^3$ is (i) a hydrogen atom, (ii) a halogen atom; (iii) a cyano group, (iv) a $C_{1-6}$ alkyl group optionally having a halogen atom or (v) a $C_{1-6}$ alkoxy group optionally having a halogen atom, and one of $R^2$ and $R^3$ is a hydrogen atom, and the other is a substituent other than a hydrogen atom, or a salt thereof [hereinafter to be sometimes abbreviated as compound (I)] unexpectedly has a very strong proton pump inhibitory effect, and is fully satisfactory as a medicament, which resulted in the completion of the present invention.

Accordingly, the present invention provides
[1] a compound represented by the formula (I)

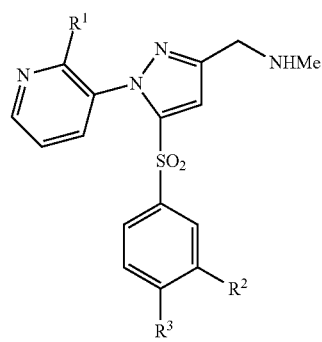

(I)

wherein $R^1$ is a substituent, $R^2$ is (i) a hydrogen atom, (ii) a $C_{1-6}$ alkyl group optionally having a halogen atom or (iii) a cyano group, $R^3$ is (i) a hydrogen atom, (ii) a halogen atom, (iii) a cyano group, (iv) a $C_{1-6}$ alkyl group optionally having a halogen atom or (v) a $C_{1-6}$ alkoxy group optionally having a halogen atom, one of $R^2$ and $R^3$ is a hydrogen atom, and the other is a substituent other than a hydrogen atom, or a salt thereof,

[2] the compound of the above-mentioned [1], wherein $R^1$ is a substituent consisting of 1-7 atoms except a hydrogen atom, or a salt thereof,

[3] the compound of the above-mentioned [1], wherein $R^1$ is a halogen atom, a cyano group, an optionally substituted $C_{1-6}$ alkyl group or an optionally substituted $C_{1-6}$ alkoxy group, or a salt thereof,

[4] the compound of the above-mentioned [1], wherein $R^2$ is a hydrogen atom, a $C_{1-6}$ alkyl group or a cyano group, or a salt thereof,

[5] the compound of the above-mentioned [1], wherein $R^3$ is a hydrogen atom, a halogen atom, a $C_{1-6}$ alkyl group or a $C_{1-6}$ alkoxy group, or a salt thereof,

[6] 1-{5-[(4-fluorophenyl)sulfonyl]-1-(2-fluoropyridin-3-yl)-1H-pyrazol-3-yl}-N-methylmethanamine or a salt thereof,

[7] 1-{1-(2-fluoropyridin-3-yl)-5-[(4-methoxyphenyl)sulfonyl]-1H-pyrazol-3-yl}-N-methylmethanamine or a salt thereof,

[8] 1-{1-(2-fluoropyridin-3-yl)-5-[(3-methylphenyl)sulfonyl]-1H-pyrazol-3-yl}-N-methylmethanamine or a salt thereof,

[9] 3-({1-(2-fluoropyridin-3-yl)-3-[(methylamino)methyl]-1H-pyrazol-5-yl}sulfonyl)benzonitrile or a salt thereof,

[10] a prodrug of the compound of the above-mentioned [1] or a salt thereof,

[11] a medicament comprising the compound of the above-mentioned [1] or a salt thereof or a prodrug thereof,

[12] the medicament of the above-mentioned [11], which is an acid secretion inhibitor,

[13] the medicament of the above-mentioned [11], which is a potassium-competitive acid blocker,

[14] the medicament of the above-mentioned [11], which is an agent for the prophylaxis or treatment of peptic ulcer, Zollinger-Ellison syndrome, gastritis, reflux esophagitis, Symptomatic Gastroesophageal Reflux Disease (Symptomatic GERD), Barrett's esophagus, Functional Dyspepsia, gastric cancer, stomach MALT lymphoma, ulcer caused by non-steroidal anti-inflammatory drug, or hyperacidity or ulcer due to postoperative stress; or a suppressant of upper gastrointestinal hemorrhage due to peptic ulcer, acute stress ulcer, hemorrhagic gastritis or invasive stress,

[15] a method for the prophylaxis or treatment of peptic ulcer, Zollinger-Ellison syndrome, gastritis, reflux esophagitis, Symptomatic Gastroesophageal Reflux Disease (Symptomatic GERD), Barrett's esophagus, Functional Dyspepsia, gastric cancer, stomach MALT lymphoma, ulcer caused by non-steroidal anti-inflammatory drug or hyperacidity or ulcer due to postoperative stress; or a method for suppressing upper gastrointestinal hemorrhage due to peptic ulcer, acute stress ulcer, hemorrhagic gastritis or invasive stress, comprising administering an effective amount of the compound of the above-mentioned [1] or a salt thereof or a prodrug thereof to a mammal, and

[16] use of the compound of the above-mentioned [1] or a salt thereof or a prodrug thereof, for the production of an agent for the prophylaxis or treatment of peptic ulcer, Zollinger-Ellison syndrome, gastritis, reflux esophagitis, Symptomatic Gastroesophageal Reflux Disease (Symptomatic GERD), Barrett's esophagus, Functional Dyspepsia, gastric cancer, stomach MALT lymphoma, ulcer caused by non-steroidal anti-inflammatory drug or hyperacidity or ulcer due to postoperative stress; or a suppressant of upper gastrointestinal hemorrhage due to peptic ulcer, acute stress ulcer, hemorrhagic gastritis or invasive stress.

Effect of the Invention

Compound (I) of the present invention shows a superior proton pump inhibitory effect. Conventional proton pump inhibitors such as omeprazole, lansoprazole and the like are converted to active forms in an acidic environment of stomach parietal cells and form a covalent bond with a cysteine residue of $H^+/K^+$-ATPase, and irreversibly inhibit the enzyme activity. In contrast, compound (I) inhibits proton pump ($H^+$-$K^+$-ATPase) activity in a reversible and competitive inhibitory manner, and consequently suppresses acid secretion. Therefore, it is sometimes called a potassium-competitive acid blocker (P-CAB), or an acid pump antagonist (APA). Compound (I) rapidly exhibits the action, shows the maximum efficacy from the initial administration, and shows less influence by genetic polymorphism (less variation among patients). Moreover, since it has substituents $R^2$ and $R^3$ at the m-position and p-position of phenyl group, respectively, it can further improve pharmacokinetics and can simultaneously impart a stronger pharmacological action and a lower cytotoxic action as compared to conventional compounds having a proton pump inhibitory action. Accordingly, the present invention can provide a clinically useful agent for the prophylaxis or treatment of peptic ulcer (e.g., gastric ulcer, duodenal ulcer, anastomotic ulcer, ulcer caused by non-steroidal anti-inflammatory drug, ulcer due to postoperative stress etc.), Zollinger-Ellison syndrome, gastritis, erosive esophagitis, reflux esophagitis, symptomatic gastroesophageal reflux disease (Symptomatic GERD), Barrett's esophagus, functional dyspepsia, gastric cancer, stomach MALT lymphoma or hyperacidity; or a suppressant of upper gastrointestinal hemorrhage due to peptic ulcer, acute stress ulcer, hemorrhagic gastritis or invasive stress; and the like. Since compound (I) shows low toxicity and is superior in water-solubility, in vivo kinetics and efficacy expression, it is useful as a pharmaceutical composition. Since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, onset of inhibitory action on gastric acid secretion is rapid, and symptoms such as pain and the like can be alleviated rapidly.

DESCRIPTION OF EMBODIMENTS

In the present specification, as the "halogen atom" or "halogen", fluorine atom, chlorine atom, bromine atom and iodine atom can be mentioned.

In the formula (I), $R^1$ is a substituent. The "substituent" is preferably a substituent consisting of 1-7 atoms except a hydrogen atom, and a halogen atom, a cyano group, an optionally substituted $C_{1-6}$ alkyl group or an optionally substituted $C_{1-6}$ alkoxy group is more preferable.

As the "$C_{1-6}$ alkyl group" of the "optionally substituted $C_{1-6}$ alkyl group" for $R^1$, methyl, ethyl, n-propyl, isopropyl, n-butyl, isobutyl, sec-butyl, tert-butyl, n-pentyl, sec-pentyl, isopentyl, neopentyl, n-hexyl, isohexyl and the like can be mentioned.

As the substituent of the "$C_{1-6}$ alkyl group", (1) a halogen atom, (2) nitro, (3) cyano, (4) hydroxy, (5) a $C_{1-6}$ alkoxy group optionally having 1 to 3 halogen atoms (e.g., methoxy, ethoxy, propoxy, isopropoxy, butoxy, isobutoxy, sec-butoxy, pentyloxy, hexyloxy, fluoromethoxy etc.), (8) mercapto, (9) $C_{1-6}$ alkylthio optionally having 1 to 3 halogen atoms (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl, etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) 5- to 7-membered saturated cyclic amino optionally containing, besides carbon atoms and one nitrogen atom, 1 or 2 kinds of 1 to 4 heteroatoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atoms, 1 or 2 kinds of 1 to 4 heteroatoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.) and the like can be mentioned, wherein the number of substituents is 1 to 5, preferably 1 to 3.

As the "$C_{1-6}$ alkoxy group" of the "optionally substituted alkoxy group" for $R^1$, methoxy, ethoxy, propoxy, isopropoxy, butoxy, isobutoxy, sec-butoxy, pentyloxy, hexyloxy and the like can be mentioned.

As the substituent of the "$C_{1-6}$ alkoxy group", those similar to the substituents recited as the substituents of the abovementioned "optionally substituted $C_{1-6}$ alkyl group" can be mentioned, wherein the number of substituents is 1 to 5, preferably 1 to 3.

$R^2$ is (i) a hydrogen atom, (ii) a $C_{1-6}$ alkyl group optionally having a halogen atom or (iii) a cyano group.

As the "$C_{1-6}$ alkyl group" of the "$C_{1-6}$ alkyl group optionally having a halogen atom" for $R^2$, those similar to the "$C_{1-6}$ alkyl group" of the "optionally substituted $C_{1-6}$ alkyl group" for $R^1$ can be mentioned, which optionally has 1 to 5, preferably 1 to 3, halogen atoms.

$R^3$ is (i) a hydrogen atom, (ii) a halogen atom, (iii) a cyano group, (iv) a $C_{1-6}$ alkyl group optionally having a halogen atom or (v) a $C_{1-6}$ alkoxy group optionally having a halogen atom.

As the "$C_{1-6}$ alkyl group optionally having a halogen atom" for $R^3$, those similar to the "$C_{1-6}$ alkyl group optionally having a halogen atom" for $R^2$ can be mentioned.

As the "$C_{1-6}$ alkoxy group" of the "$C_{1-6}$ alkoxy group optionally having a halogen atom" for $R^3$, those similar to the "$C_{1-6}$ alkoxy group" of the "optionally substituted $C_{1-6}$ alkoxy group" for $R^1$ can be mentioned, which optionally has 1 to 5, preferably 1 to 3, halogen atoms.

One of $R^2$ and $R^3$ is a hydrogen atom, and the other is a substituent other than a hydrogen atom.

$R^1$ is more preferably a halogen atom, a cyano group, a methyl group, an ethyl group, a methoxy group or an ethoxy group, more preferably a halogen atom, and a fluorine atom is particularly preferable.

$R^2$ is preferably a hydrogen atom, a $C_{1-6}$ alkyl group or a cyano group, more preferably a hydrogen atom, a methyl group or a cyano group.

$R^3$ is preferably a hydrogen atom, a halogen atom, a $C_{1-6}$ alkyl group or a $C_{1-6}$ alkoxy group, more preferably a hydrogen atom, a halogen atom, a methyl group or a methoxy group.

In another embodiment, $R^3$ is a hydrogen atom, a halogen atom or a $C_{1-6}$ alkoxy group. $R^3$ is preferably a hydrogen atom, a halogen atom or a $C_{1-3}$ alkoxy group, more preferably a hydrogen atom, a halogen atom or a methoxy group.

In the formula (I), $R^1$ is preferably a substituent consisting of 1-7 atoms except a hydrogen atom, $R^2$ is preferably a hydrogen atom, a $C_{1-6}$ alkyl group or a cyano group, $R^3$ is preferably a hydrogen atom, a halogen atom, a $C_{1-6}$ alkyl group or a $C_{1-6}$ alkoxy group, one of $R^2$ and $R^3$ is preferably a hydrogen atom, and the other is a substituent other than a hydrogen atom and, in the formula (I), $R^1$ is more preferably a halogen atom, a cyano group, an optionally substituted $C_{1-6}$ alkyl group or an optionally substituted $C_{1-6}$ alkoxy group, $R^2$ is more preferably a hydrogen atom, a $C_{1-6}$ alkyl group or a cyano group, $R^3$ is more preferably a hydrogen atom, a halogen atom, a $C_{1-6}$ alkyl group or a $C_{1-6}$ alkoxy group, one of $R^2$ and $R^3$ is more preferably a hydrogen atom, and the other is a substituent other than a hydrogen atom.

In the present invention, the following compounds are particularly preferable.

1-{5-[(4-fluorophenyl)sulfonyl]-1-(2-fluoropyridin-3-yl)-1H-pyrazol-3-yl}-N-methylmethanamine or a salt thereof.

1-{1-(2-fluoropyridin-3-yl)-5-[(4-methoxyphenyl)sulfonyl]-1H-pyrazol-3-yl}-N-methylmethanamine or a salt thereof.

1-{1-(2-fluoropyridin-3-yl)-5-[(3-methylphenyl)sulfonyl]-1H-pyrazol-3-yl}-N-methylmethanamine or a salt thereof.

3-({1-(2-fluoropyridin-3-yl)-3-[(methylamino)methyl]-1H-pyrazol-5-yl}sulfonyl)benzonitrile or a salt thereof.

Examples of the salt of compound (I) include metal salts, ammonium salts, salts with organic bases, salts with inorganic acids, salts with organic acids, salts with basic or acidic amino acids and the like. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-

In the formula, p is an integer of 0, 1 or 2 and when p is 0 or 1, the compound can be converted to a compound wherein p is 2 by oxidation using a suitable oxidant (e.g., aqueous hydrogen peroxide, 3-chloroperbenzoic acid etc.) for each compound. Compound (I) is a compound (Ia) wherein p is 2.

While the compounds obtained in respective steps can be used for the next reaction in the form of a reaction mixture or a crude product, they can also be isolated from the reaction mixture by a conventional method and easily purified by purification means, such as recrystallization, distillation, chromatography and the like.

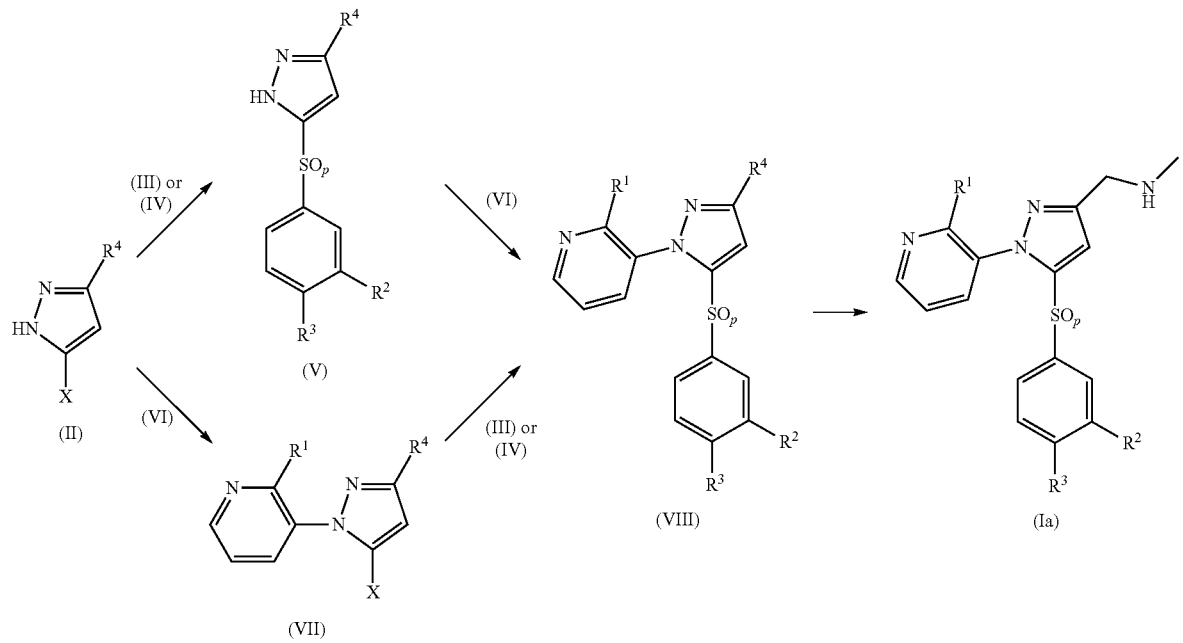

dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like. Preferable examples of the salt with acidic amino acid include a salt with aspartic acid, glutamic acid and the like.

Of these, pharmaceutically acceptable salts are preferable. For example, when a compound contains an acidic functional group, inorganic salts such as alkali metal salt (e.g., sodium salt, potassium salt etc.), alkaline earth metal salt (e.g., calcium salt, magnesium salt, barium salt etc.) and the like, ammonium salts and the like; and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like.

The production methods of compound (I) of the present invention are explained.

The compounds (Ia)-(XII) in the reaction schemes may form salts, and as such salts, for example, those similar to the salts of compound (I) can be mentioned.

Compound (II) wherein X is a hydrogen atom; a leaving group such as a halogen atom (e.g., fluorine atom, chlorine atom, bromine atom, iodine atom), methanesulfonyloxy, p-toluenesulfonyloxy, trifluoromethanesulfonyloxy and the like; a hydroxy group; an amino group or a mercapto group, and $R^4$ is a hydrogen atom, a formyl group, a carboxyl group, an ester group, a cyano group, a methylaminocarbonyl group and the like may be a commercially available product, or can be produced by a method known per se, for example, the method described in Heterocycles, vol. 46, page 489 (1997) and the like, or a method analogous thereto.

Compound (V) wherein each symbol is as defined above can be produced by, when X in compound (II) is a hydrogen atom, a leaving group such as a halogen atom (e.g., fluorine atom, chlorine atom, bromine atom, iodine atom), methanesulfonyloxy, p-toluenesulfonyloxy, trifluoromethanesulfonyloxy and the like, reacting compound (II) with compound (III)

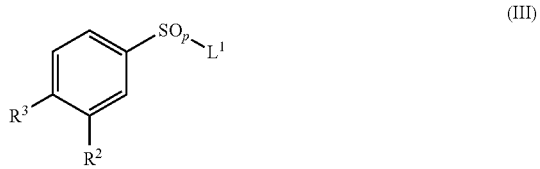

wherein $R^2$, $R^3$ and p are as defined above, and $L^1$ is a hydrogen atom, a leaving group such as a halogen atom (e.g., fluorine atom, chlorine atom, bromine atom, iodine atom) and the like, or a metal atom such as sodium, potassium and the like, or when X of compound (II) is a mercapto group, reacting compound (II) with compound (IV)

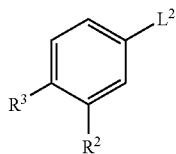
(IV)

wherein $R^2$ and $R^3$ are as defined above, and $L^2$ is a hydrogen atom or a leaving group such as a halogen atom (e.g., fluorine atom, chlorine atom, bromine atom, iodine atom), methanesulfonyl, p-toluenesulfonyl and the like.

The amount of compound (III) to be used is about 1 to about 10 mol, preferably about 1 to about 3 mol, per 1 mol of compound (II).

The amount of compound (IV) to be used is about 1 to about 10 mol, preferably about 1 to about 3 mol, per 1 mol of compound (II).

This reaction is advantageously carried out using a solvent inert to the reaction. The solvent is not particularly limited as long as the reaction proceeds. Preferable examples thereof include hydrocarbons such as benzene, toluene and the like, ethers such as tetrahydrofuran and the like, amides such as N,N-dimethylformamide, N,N-dimethylacetamide and the like, and a mixed solvent thereof and the like.

The reaction is advantageously carried out using a base. Examples of the base include inorganic bases such as sodium hydride, sodium hydroxide, potassium hydroxide and the like; basic salts such as sodium carbonate, potassium carbonate, cesium carbonate, sodium hydrogen carbonate and the like; metal bases such as potassium ethoxide, potassium tert-butoxide, sodium methoxide, sodium ethoxide and the like; aromatic amines such as pyridine, lutidine and the like; tertiary amines such as triethylamine, N-diisopropylethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like. The amount of the base to be used is about 1 to about 10 mol, preferably about 1 to about 5 mol, per 1 mol of compound (II).

This reaction can also be performed in the presence of a crown ether or a halogenating agent. Examples of the crown ether include 15-crown-5-ether, 18-crown-6-ether and the like, and examples of the halogenating agent include N-iodosuccinimide, N-bromosuccinimide, N-chlorosuccinimide, bromine and the like. The amount of the crown ether or the halogenating agent to be used is about 1 to about 10 mol, preferably about 1 to about 5 mol, per 1 mol compound (II).

This reaction can also be performed in the presence of a metal catalyst such as palladium catalyst and the like. Examples of the palladium catalyst include tetrakis(triphenylphosphine)palladium(0), tris(dibenzylideneacetone)dipalladium, palladium acetate and the like. In this case, this reaction can also be performed in the co-presence of phosphines when desired. Examples of phosphines include 9,9-dimethyl-4,5-bis(diphenylphosphino)xanthine (XANTPHOS), 2,2'-bis(diphenylphosphino)-1,1'-binaphthyl (BINAP) and the like. The amount of the palladium catalyst or phosphine to be used is about 0.01 to about 0.5 mol, preferably about 0.01 to about 0.3 mol, per 1 mol of compound (II).

While the reaction time varies depending on the reagent and solvent to be used, it is generally about 30 min to about 24 hr, preferably about 30 min to about 18 hr.

The reaction temperature is generally about 0° C. to about 150° C., preferably about 10° C. to about 120° C.

Compound (VII) wherein each symbol is as defined above may be a commercially available product, or can be produced by a method known per se, for example, the method described in Bioorganic and Medicinal Chemistry Letters, vol. 16, page 731 (2006), Chemical and Pharmaceutical Bulletin, vol. 31, page 1228 (1983), WO2004/98589 and the like, or a method analogous thereto. In addition, it can be produced by reacting compound (II) with compound (VI)

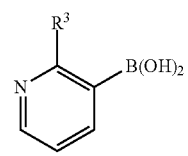
(VI)

wherein each symbol is as defined above (or various ester derivatives of compound (VI)), by the method described in Tetrahedron Letters, vol. 39, page 2941 (1998), or a method analogous thereto.

The amount of compound (VI) to be used is about 1 to about 10 mol, preferably about 1 to about 3 mol, per 1 mol of compound (II).

Compound (VIII) can be produced from compound (V) by a method similar to the method of producing compound (VII) from compound (II), or a method analogous thereto. It can also be produced from compound (VII) by a method similar to the method of producing compound (V) from compound (II), or a method analogous thereto.

Compound (Ia) can be produced, when $R^4$ of compound (VIII) is a formyl group, by a reductive amination reaction using compound (IX)

 Me-NH$_2$ (IX)

wherein Me is a methyl group, according to the method described in Shinjikken Kagaku Kouza (Courses in Experimental Chemistry), vol. 14-III, pages 1380-1385 (Maruzen Press) or the like.

The amount of compound (IX) to be used is about 1 to about 20 mol, preferably about 1 to about 10 mol, per 1 mol of compound (VIII).

Compound (Ia) can be produced by, when $R^4$ of compound (VIII) is a hydrogen atom, for example, formylation by the method described in Jikken Kagaku Kouza, 4$^{th}$ ed. vol. 21, pages 106 to 124 (1991) (Maruzen Press) and the like or a method analogous thereto, followed by the reductive amination mentioned earlier.

Furthermore, compound (Ia) can be produced by, when $R^4$ of compound (VIII) is an ester group, reduction of the ester group with a reducing agent such as lithium aluminum hydride, diisobutylaluminum hydride, sodium borohydride, calcium bis(borohydride) and the like, reaction of the resulting hydroxy group with an oxidant such as chromic acid-pyridine complex, pyridinium chlorochromate, manganese dioxide, sulfur trioxide-pyridine complex or tetra-n-propylammonium perruthenate and the like to convert to a formyl group, followed by the reductive amination mentioned earlier.

As the reducing agent, diisobutylaluminum hydride is particularly preferable. The amount of the reducing agent to be used is about 0.75 to about 10 equivalents, preferably about 1 to about 5 equivalents, per 1 mol of compound (VIII).

Preferable examples of the oxidant include manganese dioxide, sulfur trioxide-pyridine complex and tetra-n-propylammonium perruthenate. The amount of the oxidant to be used is about 0.01 to about 30 equivalents, preferably about 0.05 to about 10 equivalents, per 1 mol of compound (VIII). The oxidation reaction can be performed, for example, according to the method described in Synthesis, page 639 (1994).

This reaction is advantageously performed using a solvent inert to the reaction. Such solvent is not particularly limited as long as the reaction proceeds, and hydrocarbons such as benzene, toluene and the like and ethers such as tetrahydrofuran, diethyl ether and the like or a mixed solvent thereof and the like are preferable.

While the reaction time varies depending on the reagent and solvent to be used, it is generally about 30 min to about 24 hr, preferably about 30 min to about 8 hr.

The reaction temperature is generally about −78° C. to about 100° C., preferably about −78° C. to about 25° C.

Also, compound (Ia) can be produced by, when $R^4$ of compound (VIII) is a cyano group, reduction with a reducing agent such as diisobutylaluminum hydride and the like to convert to a formyl group, followed by the reductive amination mentioned earlier.

As the reducing agent, diisobutyl aluminum hydride is particularly preferable. The amount of the reducing agent to be used is about 0.75 to about 10 equivalents, preferably about 1 to about 5 equivalents, per 1 mol of compound (VIII).

This reaction is advantageously performed using a solvent inert to the reaction. Such solvent is not particularly limited as long as the reaction proceeds, and hydrocarbons such as benzene, toluene and the like and ethers such as tetrahydrofuran, diethyl ether and the like or a mixed solvent thereof and the like are preferable.

While the reaction time varies depending on the reagent and solvent to be used, it is generally about 30 min to about 24 hr, preferably about 30 min to about 8 hr.

The reaction temperature is generally about −78° C. to about 100° C., preferably about −78° C. to about 25° C.

Furthermore, compound (Ia) can be produced by, when $R^4$ of compound (VIII) is a methylaminocarbonyl group, reduction with a reducing agent.

As the reducing agent, metal hydrides such as sodium borohydride, lithium aluminum hydride and the like, boranes such as borane tetrahydrofuran complex and the like, and the like are used. The amount of the reducing agent to be used is about 0.5 to about 10 mol, preferably about 1 to about 5 mol, per 1 mol of compound (VIII). When desired, an acid catalyst may be added along with the reducing agent.

As the acid catalyst, Lewis acids such as trifluoroborane diethyl ether complex, aluminum chloride and the like, and the like are used. The amount of the acid catalyst to be used is about 0.5 to about 10 mol, preferably about 1.0 to about 5.0 mol, relative to compound (VIII).

This reaction is advantageously performed without solvent, or in a solvent inert to the reaction. Such solvent is not particularly limited as long as the reaction proceeds. For example, alcohols such as methanol, ethanol, propanol and the like, hydrocarbons such as cyclohexane, hexane, benzene, toluene, xylene, mesitylene and the like, organic acids such as formic acid, acetic acid and the like, ethers such as tetrahydrofuran, dioxane, 1,2-dimethoxyethane, diethyl ether, diisopropyl ether and the like, anilines such as N,N-dimethylaniline, N,N-diethylaniline and the like, halogenated hydrocarbons such as dichloromethane, chloroform, carbon tetrachloride, 1,2-dichloroethane and the like or a mixed solvent thereof and the like are used.

The reaction time is generally about 10 min to about 24 hr, preferably about 30 min to 12 hr. The reaction temperature is generally about 0 to about 120° C., preferably about 25 to about 100° C.

Furthermore, compound (Ia) can be produced by, when $R^4$ of compound (VIII) is an ester group or a carboxyl group, condensation with compound (IX), followed by the reduction mentioned earlier.

The aforementioned reaction may be performed in the presence of a suitable condensing agent.

Examples of the condensing agent include N,N'-carbodiimides such as N,N'-dicyclohexylcarbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, acetic anhydride and the like; 2-halogenopyridiniums such as 2-chloromethylpyridinium iodide, 2-fluoro-1-chloromethylpyridinium iodide and the like, and the like. The amount of the condensing agent to be used is about 1 to about 5 mol, preferably about 2 to 3 mol, per 1 mol of compound (VIII).

When desired, the reaction may be performed in the co-presence of a base along with the condensing agent. As the base, basic salts such as potassium acetate, sodium acetate and the like, 1-hydroxy-1H-benzotriazole (HOBt) monohydrate and the like can be mentioned. The amount of the base to be used is about 1 to about 5 mol, preferably about 2 to about 3 mol, per 1 mol of compound (VIII).

This reaction is advantageously performed using a solvent inert to the reaction. Preferable examples of the solvent include alcohols such as methanol, ethanol, propanol and the like, hydrocarbons such as cyclohexane, hexane, benzene, toluene, xylene and the like, ethers such as tetrahydrofuran, dioxane, 1,2-dimethoxyethane, diethyl ether, diisopropyl ether and the like, amides such as N,N-dimethylformamide, N,N-dimethylacetamide, hexamethylphosphoric triamide and the like, sulfoxides such as dimethyl sulfoxide and the like, halogenated hydrocarbons such as dichloromethane, chloroform, carbon tetrachloride, 1,2-dichloroethane and the like, acid anhydrides such as acetic anhydride and the like or a mixed solvent thereof and the like.

The reaction time is generally about 30 min to about 48 hr, preferably about 30 min to about 24 hr. The reaction temperature is generally about 0 to about 120° C., preferably about 25 to about 100° C.

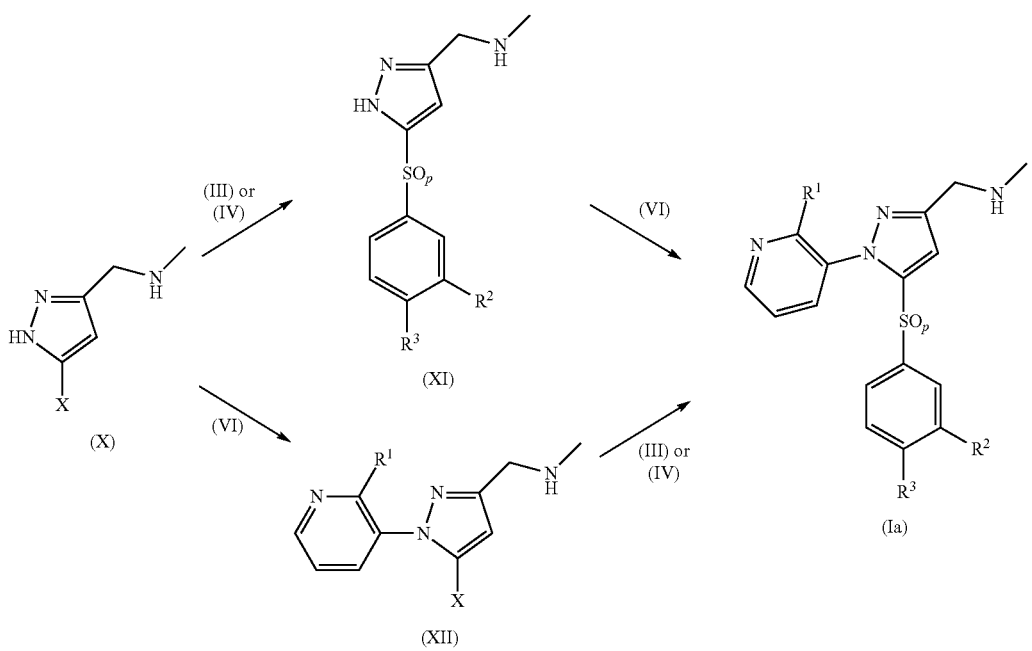

Compound (X) wherein X is as defined above may be a commercially available product or can be produced by a method known per se, for example, the method described in Journal of American Chemical. Society, vol. 72, page 745 (1950) and the like, or a method analogous thereto.

Compound (XI) can be produced from compound (X) according to a method similar to the method of producing compound (V) from compound (II), or a method analogous thereto.

Compound (XII) can be produced from compound (X) according to a method similar to the method of producing compound (VII) from compound (II), or a method analogous thereto.

Alternatively, compound (X) can be produced from compound (II) according to a method similar to the method of producing compound (Ia) from compound (VIII), or a method analogous thereto, compound (XI) can be produced from compound (V) according to a method similar to the method of producing compound (Ia) from compound (VIII), or a method analogous thereto, and compound (XII) can be produced from compound (VII) according to a method similar to the method of producing compound (Ia) from compound (VIII), or a method analogous thereto.

Compound (Ia) can be produced from compound (XI) according to a method similar to the method of producing compound (VII) from compound (II), or a method analogous thereto, or can be produced from compound (XII) according to a method similar to the method of producing compound (V) from compound (II), or a method analogous thereto.

In each of the aforementioned reactions, when the starting compound has an amino group, a carboxyl group or a hydroxyl group as a substituent, a protecting group generally used in peptide chemistry and the like may be introduced into these groups. By removing the protecting group as necessary after the reaction, the objective compound can be obtained. Introduction or removal of these protective groups may be carried out according to a method known per se, for example, the method disclosed in Theodora W. Greene and Peter G. M. Wuts, "Protective Groups in Organic Synthesis, 3$^{rd}$ Ed.", Wiley-Interscience (1999), or the like.

In any of compounds (Ia) to (XII) in the formula, when desired, compound (I) can be synthesized by performing protection-deprotection, acylation reaction, alkylation reaction, hydrogenation reaction, oxidation reaction, reduction reaction, carbon chain extension reaction and substituent exchange reaction, each singly or in a combination of two or more kinds thereof.

In any of compounds (Ia) to (XII) in the formula, when the compound is obtained as a free compound, it can be converted to an objective salt by a method known per se or a method analogous thereto. Conversely, when the compound is obtained as a salt, it can be converted to a free form or an objective other salt by a method known per se or a method analogous thereto.

Compound (I) can be isolated and purified by a known method, for example, phase transfer, concentration, solvent extraction, fractionation, liquid conversion, crystallization, recrystallization, chromatography and the like.

When compound (I) is obtained as a free compound, it can be converted to a desired salt by a method known per se or a method analogous thereto; conversely, when compound (I) is obtained as a salt, it can be converted into a free form or another desired salt by a method known per se or a method analogous thereto.

Compound (I) may be used as a prodrug. The prodrug of compound (I) means a compound which is converted to compound (I) under the physiological condition in the body by a reaction with an enzyme, gastric acid, or the like, that is, a compound which is converted to compound (I) by enzymatic oxidation, reduction, hydrolysis, and the like; a compound which is converted to compound (I) by hydrolysis with gastric acid, and the like.

Examples of the prodrug of compound (I) include a compound wherein the amino group of compound (I) is modified with acyl, alkyl or phosphoryl (e.g., a compound wherein the amino group of compound (I) is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein the hydroxy group of compound (I) is modified with acyl, alkyl, phosphoric acid or boric acid (e.g., a compound wherein the hydroxy group of compound (I) is modified with acetyl, palmitoyl, propanoyl, pivaloyl, succinyl, fumaryl, alanyl or dimethylaminomethylcarbonyl, etc.); a compound wherein a carboxyl group of compound (I) is modified to ester or amide (e.g., a compound wherein a carboxyl group of compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These compounds can be produced from compound (I) by a method known per se.

In addition, the prodrug of compound (I) may be a compound, which is converted to compound (I) under the physiological conditions, as described in Pharmaceutical Research and Development, Vol. 7 (Molecule Design), pp. 163-198 (1990), published by Hirokawa Publishing Co.

When compound (I) contains an isomer such as an optical isomer, a stereoisomer, a regioisomer or a rotamer, either isomer or a mixture of these are also encompassed in compound (I). For example, when compound (I) has an optical isomer, an optical isomer resolved from a racemate is also encompassed in compound (I). These isomers can be obtained as single products according to synthesis and separation methods known per se (concentration, solvent extraction, column chromatography, recrystallization, etc.)

The compound (I) may be a crystal, and both a single crystal and crystal mixtures are encompassed in compound (I). Crystals can be produced by crystallization according to crystallization methods known per se.

The compound (I) may be a solvate (e.g., hydrate etc.) or a non-solvate, both of which are encompassed in the compound (I).

A compound labeled with an isotope (e.g., $^3$H, $^{14}$C, $^{35}$S, $^{125}$I and the like) and a deuterium conversion form wherein $^1$H has been converted to $^2$H(D) are also encompassed in the compound (I).

Compound (I) and a prodrug thereof of the present invention (hereinafter sometimes to be abbreviated as the compound of the present invention) have a proton pump inhibitory effect and effectively suppress gastric acid secretion. In addition, since they show low toxicity (e.g., acute toxicity, chronic toxicity, genetic toxicity, reproductive toxicity, cardiotoxicity, drug interaction, carcinogenicity and the like) and high water-solubility, and are superior in the stability, in vivo kinetics (absorbability, distribution, metabolism, excretion and the like), and efficacy expression, they are useful as medicaments.

The compound of the present invention is useful for the prophylaxis or treatment of peptic ulcer (e.g., gastric ulcer, duodenal ulcer, anastomotic ulcer, ulcer caused by non-steroidal anti-inflammatory drug, ulcer due to postoperative stress etc.); Zollinger-Ellison syndrome; gastritis; erosive esophagitis; reflux esophagitis such as erosive reflux esophagitis and the like; symptomatic gastroesophageal reflux disease (Symptomatic GERD) such as nonerosive esophageal reflux, esophageal reflux unaccompanied by esophagitis and the like; Barrett's esophagus; functional dyspepsia; gastric cancer (including gastric cancer associated with promoted production of interleukin-1β due to gene polymorphism of interleukin-1); stomach MALT lymphoma; hyperacidity; upper gastrointestinal hemorrhage caused by peptic ulcer, acute stress ulcer, hemorrhagic gastritis, invasive stress (e.g., stress caused by major surgery requiring post-operative intensive management, or cerebrovascular disorder, head trauma, multiple organ failure or extensive burn requiring intensive treatment) and the like; airway disorders; asthma; and the like in mammals (e.g., human, monkey, sheep, bovine, horse, dog, cat, rabbit, rat, mouse etc.), pre-anesthetic administration, eradication or assistant to eradication of *Helicobacter pylori* and the like. As used herein, the above-mentioned reflux esophagitis (erosive esophagitis) and symptomatic gastroesophageal reflux disease (symptomatic GERD) are sometimes collectively referred to simply as GERD.

The content of a compound of the present invention in the pharmaceutical composition of the present invention is about 0.01 to 100% by weight relative to the entire composition. Though subject to change depending on the administration target, administration route, target disease and the like, its dose is about 0.5 to 1,500 mg/day, preferably about 5 to 150 mg/day, based on the active ingredient, when, for example, the compound is orally administered as an anti-ulcer agent to an adult human (60 kg). The compound of the present invention may be administered once daily or in 2 or 3 divided portions per day.

The compound of the present invention shows low toxicity and can be safely administered orally or parenterally (e.g., topical, rectal, intravenous administrations and the like) as it is or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, orally disintegrating film, liquid, injection, suppository, sustained-release preparation, plaster and the like. Particularly, the compound of the present invention is preferably administered as an oral preparation in the form of tablet, granule, capsule and the like.

Examples of the pharmacologically acceptable carrier that may be used to produce the pharmaceutical composition of the present invention include various organic or inorganic carrier substances in common use as pharmaceutical materials, including excipients, lubricants, binders, disintegrants, aqueous polymers and basic inorganic salts for solid preparations; and solvents, solubilizing agents, suspending agents, isotonizing agents, buffers and soothing agents for liquid preparations and the like. Ordinary pharmaceutical additives such as preservatives, anti-oxidants, colorants, sweetening agents, souring agents, bubbling agents and flavorings may also be used as necessary. Examples of the "excipients" include lactose, sucrose, D-mannitol, starch, corn starch, crystalline cellulose, light anhydrous silicic acid, titanium oxide and the like. Examples of the "lubricants" include magnesium stearate, sucrose ester of fatty acids, polyethylene glycol, talc, stearic acid and the like. Examples of the "binders" include hydroxypropyl cellulose, hydroxypropylmethyl cellulose, crystalline cellulose, starch, polyvinylpyrrolidone, gum arabic powder, gelatin, pullulan, low-substituted hydroxypropyl cellulose and the like. Examples of the "disintegrants" include (1) crosspovidone, (2) what is called super-disintegrants such as crosscarmellose sodium (manufactured by FMC-Asahi Chemical) and carmellose calcium (manufactured by GOTOKU CHEMICAL CO., LTD.) etc, (3) sodium carboxymethyl starch (e.g., product of Matsutani Chemical), (4) low-substituted hydroxypropyl cellulose (e.g., product of Shin-Etsu Chemical), (5) corn starch, and so forth. Said "crosspovidone" may be polyvinylpyrrolidone (PVPP), any crosslinked polymer having the chemical name 1-ethenyl-2-pyrrolidinone homopolymer, including 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like. Examples of the "aqueous polymers" include ethanol-soluble aqueous polymers [e.g., cellulose derivatives such as hydroxypropyl cellulose (hereinafter also referred to as HPC) etc, polyvinylpyrrolidone and the like], ethanol-insoluble aqueous polymers [e.g., cellulose derivatives such as hydroxypropylmethyl cellulose (hereinafter also referred to as HPMC) and the like, methyl cellulose, carboxymethyl cellulose sodium and the like, sodium polyacrylate, polyvinyl alcohol, sodium alginate, guar gum and the like] and the like. Examples of the "basic inorganic salts" include basic inorganic salts of sodium, potassium, magnesium and/or calcium. Preferred are basic inorganic salts of magnesium and/or calcium. More preferred are basic inorganic salts of magnesium. Examples of the basic inorganic salts of sodium include sodium carbonate, sodium hydrogen carbonate, disodium hydrogen phosphate and the like. Examples of the basic inorganic salts of potassium include potassium carbonate, potassium hydrogen carbonate and the like. Examples of the basic inorganic salts of magnesium include heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}.CO_3.4H_2O$], and aluminum magnesium hydroxide. Preferred are heavy magnesium carbonate, magnesium carbonate, magnesium oxide, magnesium hydroxide and the like. Examples of the basic inorganic salts of calcium include precipitated calcium carbonate, calcium hydroxide and the like. Examples of the "solvents" include water for injection, alcohol, propylene glycol, macrogol, sesame oil, corn oil, olive oil and the like. Examples of the "solubilizing agents" include polyethylene glycol, propylene glycol, D-mannitol, benzyl benzoate, ethanol, trisaminomethane, cholesterol, triethanolamine, sodium carbonate, sodium citrate and the like. Examples of the "suspending agents" include surfactants such as stearyltriethanolamine, sodium lauryl sulfate, laurylaminopropionic acid, lecithin, benzalkonium chloride, benzethonium chloride, glyceryl monostearate etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose and the like, and the like. Examples of the "isotonizing agents" include glucose, D-sorbitol, sodium chloride, glycerol, D-mannitol and the like. Examples of the "buffers" include buffer solutions of phosphates, acetates, carbonates, citrates and the like, and the like. Examples of the "soothing agents" include benzyl alcohol and the like. Examples of the "preservatives" include p-oxybenzoic acid esters, chlorobutanol, benzyl alcohol, phenethyl alcohol, dehydroacetic acid, sorbic acid and the like. Examples of the "antioxidants" include sulfites, ascorbic acid, α-tocopherol and the like. Examples of the "colorants" include food colors such as Food Color Yellow No. 5, Food Color Red No. 2, Food Color Blue No. 2 and the like; food lake colors, red ferric oxide and the like. Examples of the "sweetening agents" include saccharin sodium, dipotassium glycyrrhizinate, aspartame, stevia, thaumatin and the like. Examples of the "souring agents" include citric acid (citric anhydride), tartaric acid, malic acid and the like. Examples of the "bubbling agents" include sodium bicarbonate and the like. The "flavorings" may be synthetic substances or naturally occurring substances, and examples thereof include lemon, lime, orange, menthol, strawberry and the like.

The compound of the present invention may be prepared as a preparation for oral administration in accordance with a commonly-known method, by, for example, compression-shaping with a carrier such as an excipient, a disintegrant, a binder, a lubricant, or the like, and subsequently coating the preparation as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the compound of the present invention as an orally disintegrating tablet, available methods include a method in which a core containing crystalline cellulose and lactose is coated with the compound of the present invention and, where necessary, a basic inorganic salt, and then further coated with a coating layer containing an aqueous polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

Examples of the above-mentioned "enteric coating layer" include a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., Eudragit L30D-55 (trade name; produced by Rohm), Colicoat MAE30DP (trade name; produced by BASF), Polyquid PA30 (trade name; produced by San-yo Chemical) etc.), carboxymethylethyl cellulose, shellac and the like; sustained-release substrates such as methacrylic acid copolymers (e.g., Eudragit NE30D (trade name), Eudragit RL30D (trade name), Eudragit RS30D (trade name), etc.) and the like; aqueous polymers; plasticizers such as triethyl citrate, polyethylene glycol, acetylated monoglycerides, triacetin, castor oil and the like; and the like, and the like.

Examples of the above-mentioned "additive" include aqueous sugar alcohols (e.g., sorbitol, mannitol, maltitol, reduced starch saccharides, xylitol, reduced palatinose, erythritol, etc.), crystalline cellulose (e.g., Ceolas KG 801, Avicel PH 101, Avicel PH 102, Avicel PH 301, Avicel PH 302, Avicel RC-591 (crystalline cellulose-carmellose sodium) etc.), low-substituted hydroxypropyl cellulose (e.g., LH-22, LH-32, LH-23, LH-33 (Shin-Etsu Chemical), mixtures thereof etc.) and the like. Furthermore, binders, souring agents, bubbling agents, sweetening agents, flavorings, lubricants, colorants, stabilizers, excipients, disintegrants and the like are also used.

The compound of the present invention may be used in combination with 1 to 3 other active ingredients. Examples of the "other active ingredients" include anti-*Helicobacter pylori* active substances, imidazole compounds, bismuth salts, quinolone compounds, and so forth. Examples of the "anti-*Helicobacter pylori* active substance" include penicillin antibiotic (e.g., amoxicillin, benzylpenicillin, piperacillin, mecillinam, ampicillin, temocillin, bacampicillin, aspoxicillin, sultamicillin, lenampicillin etc.), cephem antibiotic (e.g., cefixime, cefaclor etc.), macrolide antibiotic (e.g., erythromycin, clarithromycin, roxithromycin, rokitamycin, flurithromycin, telithromycin etc.), tetracycline antibiotic (e.g., tetracycline, minocycline, streptomycin etc.), aminoglycoside antibiotic (e.g., gentamicin, amikacin etc.), imipenem and the like. Of these, penicillin antibiotic, macrolide antibiotic and the like are preferable. Examples of the "imidazole compounds" include metronidazole, miconazole and the like. Examples of the "bismuth salts" include bismuth acetate, bismuth citrate, bismuth subsalicylate and the like. Examples of the "quinolone compounds" include ofloxacin, ciploxacin and the like. For eradication of *Helicobacter pylori*, a compound (I) of the present invention with antibiotic penicillin (e.g., amoxicillin and the like) and antibiotic erythromycin (e.g., clarithromycin and the like) is preferably used.

For the purpose of eradication of *Helicobacter pylori*, while the compound of the present invention has an anti-*H. pylori* action (bacteriostatic action or eradication action) by itself, it can enhance antibacterial action of other antibiotics based on the pH controlling action in the stomach and the like, and also provides an assistant effect such as an eradication effect based on the action of the antibiotics to be used in combination. The "other active ingredients" and the compound (I) of the present invention may be mixed, prepared as a single pharmaceutical composition [e.g., tablets, powders, granules, capsules (including soft capsules), liquids, injectable preparations, suppositories, sustained-release preparations, etc.], in accordance with a commonly known method, and used in combination, and may also be prepared as separate preparations and administered to the same subject simultaneously or at a time interval.

In addition, the compound of the present invention may be used in combination with a gastric motility enhancer, a drug acting on lower esophageal sphincter (e.g., temporary lower esophageal sphincter relaxation suppressant etc.), ClC-2 channel opener (intestinal juice secretion enhancer), a histamine $H_2$ receptor antagonist, an antacid, a sedative, a stomachic digestant or a non-steroidal anti-inflammatory drug (NSAID). Examples of the "gastric motility enhancer" include domperidone, metoclopramide, mosapride, itopride, tegaserod and the like. Examples of the "a drug acting on lower esophageal sphincter" include GABA-B receptor agonists such as baclofen, an optically active form thereof and the like, glutamine receptor antagonists and the like. Examples of the "ClC-2 channel opener (intestinal juice secretion enhancer)" include lubiprostone and the like. Examples of the "histamine $H_2$ receptor antagonist" include cimetidine, ranitidine, famotidine, roxatidine, nizatidine, lafutidine and the like. Examples of the "antacid" include sodium hydrogen carbonate, aluminum hydroxide and the like. Examples of the "sedatives" include diazepam, chlordiazepoxide and the like. Examples of the "stomachic digestant" include gentiana, swertia japonica, diastase and the like. Examples of the "non-steroidal anti-inflammatory drug" include aspirin, indomethacin, ibuprofen, mefenamic acid, diclofenac, etodorac, piroxicam, celecoxib and the like.

A gastric motility enhancer, a drug acting on lower esophageal sphincter, a ClC-2 channel opener (intestinal juice secretion enhancer), a histamine $H_2$ receptor antagonist, an antacid, a sedative, a stomachic digestant or a non-steroidal anti-inflammatory drug and compound (I) of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

The compound of the present invention may be used in combination with the following drugs.

(i) proton pump inhibitor, for example, omeprazole, esomeprazole, pantoprazole, rabeprazole, tenatoprazole, ilaprazole and lansoprazole;

(ii) oral antacid combination agent, for example, Maalox, Aludrox and Gaviscon;

(iii) mucosaprotector, for example, polaprezinc, ecabe sodium, rebamipide, teprenone, cetraxate, sucralfate, chloropylline-copper and plaunotol;

(iv) antigastric agent, for example, anti-gastrin vaccine, itriglumide and Z-360;

(v) 5-$HT_3$ antagonist, for example, dolasetron, palonosetron, alosetron, azasetron, ramosetron, mitrazapine, granisetron, tropisetron, E-3620, ondansetron and indisetron;

(vi) 5-$HT_4$ agonist, for example, tegaserod, mosapride, cinitapride and oxtriptane;

(vii) laxative agent, for example, Trifyba, Fybogel, Konsyl, Isogel, Regulan, Celevac and Normacol;

(viii) $GABA_B$ agonist, for example, baclofen and AZD-3355;

(ix) $GABA_B$ antagonist, for example, GAS-360 and SGS-742;

(x) calcium channel blocker, for example, aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonist, for example, metoclopramide, domperidone and levosulpiride;

(xii) tachykinin (NK) antagonist, particularly, NK-3, NK-2 and NK-1 antagonist, for example, nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S);

(xiii) nitric monoxide synthase inhibitor, for example, GW-274150, tilarginine, P54, guanidioethyldisulfide and nitroflurbiprofen;

(xiv) vanilloid receptor 1 antagonist, for example, AMG-517 and GW-705498;

(xv) ghrelin agonist, for example, capromorelin and TZP-101;

(xvi) AchE release stimulant, for example, Z-338 and KW-5092.

The above-mentioned drugs (i)-(xvi) and compound (I) of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

EXAMPLES

The present invention is explained in detail in the following by referring to Reference Examples, Examples and Experimental Examples, which are not to be construed as limitative.

In the following Reference Examples and Examples, the "room temperature" generally means about 10° C. to about 35° C., but it is not particularly strictly limited. The mixing ratio of liquids shows a volume ratio. Unless otherwise specified, "%" means weight %. The yield is in mol/mol %. Silica gel column chromatography was performed using silica gel 60 (0.063-0.200 mm) manufactured by MERCK, Fuji Silysia Chemical Ltd. Chromatorex (trade name) NH (described as basic silica gel column chromatography) or Purif-Pack manufactured by MORITEX (described as silica gel column chromatography or basic silica gel column chromatography). The melting point was measured using Yanagimoto trace melting point measurement apparatus or Buechi trace melting point measurement apparatus (B-545), and shown without amendment. For $^1$H-NMR spectrum, tetramethylsilane was used as the internal standard, and Varian Gemini-200 (200 MHz), Mercury-300 (300 MHz) spectrometer, Bruker AVANCE AV300 (300 MHz) and JNM-AL400 (400 MHz) nuclear magnetic resonance apparatuses JEOL DATUM (JEOL DATUM LTD.) were used for the measurement. The following abbreviations are used for showing the measurement results.

s: singlet, doublet, dd: double doublet, ddd: triple doublet, dt: double triplet, t: triplet, q: quartet, dq: double quartet, m: multiplet, br: broad, brs: broad singlet, J: coupling constant, Hz: Hertz.

Reference Example 1 ethyl 1-(2-fluoropyridin-3-yl)-5-hydroxy-1H-pyrazole-3-carboxylate

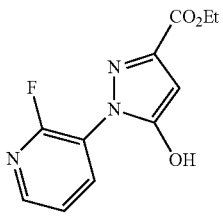 [SMILES: CCOC(=O)c1cc(O)n(-c2cccnc2F)n1]

To a solution of 2-fluoro-3-hydrazinopyridine (30.0 g) in ethanol (472 mL) were added sodium carbonate (65.2 g) and diethyl but-2-ynedioate (40.2 g). After refluxing for 18 hr, the mixture was cooled to room temperature, treated with 2 mol/L hydrochloric acid, and extracted twice with ethyl acetate. The extract was dried over anhydrous sodium sulfate and concentrated under reduced pressure. The residue was suspended in diethyl ether, and the obtained solid was collected by filtration and dried under reduced pressure to give the title compound as a yellow solid (yield 20.0 g, yield 34%).

$^1$H-NMR (DMSO-$d_6$) δ: 1.28 (3H, t, J=7.2 Hz), 4.23 (2H, q, J=7.2 Hz), 5.94 (1H, s), 7.57 (1H, ddd, J=7.6, 4.8, 1.2 Hz), 7.49 (1H, ddd, J=9.6, 7.6, 1.6 Hz), 8.39 (1H, dt, J=4.8, 1.6 Hz), 12.3 (1H, brs).

Reference Example 2 ethyl 1-(2-fluoropyridin-3-yl)-5-{[(trifluoromethyl)sulfonyl]oxy}-1H-pyrazole-3-carboxylate

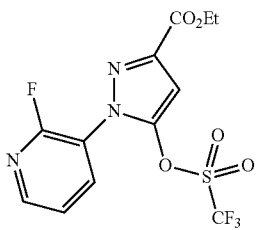 [SMILES: CCOC(=O)c1cc(OS(=O)(=O)C(F)(F)F)n(-c2cccnc2F)n1]

To a solution of ethyl 1-(2-fluoropyridin-3-yl)-5-hydroxy-1H-pyrazole-3-carboxylate (2.0 g) in tetrahydrofuran (20 mL) were added triethylamine (966 mg) and N-phenylbis(trifluoromethanesulfonimide) (3.1 g). After stirring at room temperature for 15 min, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=19:1→9:1) to give the title compound as a yellow oil (yield 2.1 g, yield 70%).

$^1$H-NMR CDCl$_3$) δ: 1.43 (3H, t, J=7.2 Hz), 4.46 (2H, q, J=7.2 Hz), 6.88 (1H, s), 7.40-7.45 (1H, m), 7.99-8.06 (1H, m), 8.40-8.43 (1H, m).

Reference Example 3 ethyl 5-[(4-fluorophenyl)sulfanyl]-1-(2-fluoropyridin-3-yl)-1H-pyrazole-3-carboxylate

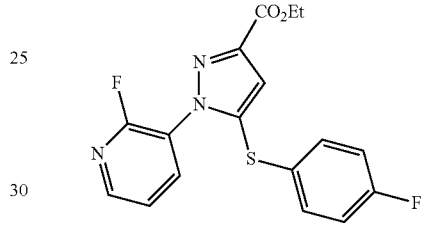

A solution of ethyl 1-(2-fluoropyridin-3-yl)-5-{[(trifluoromethyl)sulfonyl]oxy}-1H-pyrazole-3-carboxylate (353 mg), 4-fluorobenzenethiol (130 mg) and sodium carbonate (146 mg) in toluene (5 mL) was sufficiently deaerated. Tris(dibenzylideneacetone)dipalladium(0) (8.4 mg) and 4,5-bis(diphenylphosphino)-9,9-dimethylxanthene (11 mg) were added and the mixture was further deaerated. The mixture was stirred under an argon atmosphere at 110° C. for 3 hr, allowed to cool to room temperature, ethyl acetate was added, and the mixture was filtered through a silica gel pad. The organic layer of the filtrate was washed with saturated brine, dried over anhydrous sodium sulfate, and concentrated under reduced pressure. The residue was silica gel column chromatography (eluent:hexane-ethyl acetate=19:1→2:1) to give the title compound as a crude yellow oil (yield 203 mg).

Reference Example 4 ethyl 5-[(4-fluorophenyl)sulfonyl]-1-(2-fluoropyridin-3-yl)-1H-pyrazole-3-carboxylate

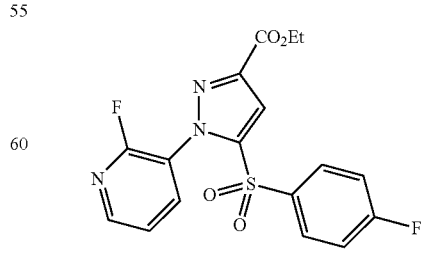

To a solution of crude ethyl 5-[(4-fluorophenyl)sulfanyl]-1-(2-fluoropyridin-3-yl)-1H-pyrazole-3-carboxylate (203 mg) in ethyl acetate (3 mL) was added 3-chloroperbenzoic acid (596 mg). The mixture was stirred at room temperature for 2 hr, treated with saturated aqueous sodium thiosulfate solution, and extracted with ethyl acetate. The extract was washed with water, saturated aqueous sodium hydrogen carbonate solution and saturated brine, dried over anhydrous sodium sulfate, and concentrated under reduced pressure. The residue was purified by basic silica gel column chromatography (eluent:hexane-ethyl acetate=9:1→2:1) to give the title compound as a colorless oil (yield 171 mg, 2 step yield 47%).

$^1$H-NMR (CDCl$_3$) δ: 1.41 (3H, t, J=7.2 Hz), 4.44 (2H, q, J=7.2 Hz), 7.10-7.20 (2H, m), 7.40 (1H, ddd, J=7.8, 4.9, 0.9 Hz), 7.54-7.65 (3H, m), 7.93 (1H, ddd, J=9.2, 7.5, 1.9 Hz), 8.41 (1H, dt, J=4.9, 1.5 Hz).

Reference Example 5

{5-[(4-fluorophenyl)sulfonyl]-1-(2-fluoropyridin-3-yl)-1H-pyrazol-3-yl}methanol

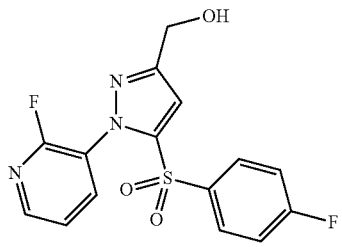 [SMILES: O=S(=O)(c1ccc(F)cc1)c1cc(CO)nn1-c1cccnc1F]

A solution of ethyl 5-[(4-fluorophenyl)sulfonyl]-1-(2-fluoropyridin-3-yl)-1H-pyrazole-3-carboxylate (170 mg) in tetrahydrofuran (2.5 mL) was cooled to −78° C., and a 1.5 mol/L solution (1.2 mL) of diisobutylaluminum hydride in toluene was added dropwise. The reaction mixture was stirred at room temperature for 1 hr, treated with 1 mol/L hydrochloric acid, and extracted with ethyl acetate. The extract was washed with water, saturated aqueous sodium hydrogen carbonate solution and saturated brine, dried over anhydrous sodium sulfate, and concentrated under reduced pressure to give the title compound as a yellow solid (yield 135 mg, yield 89%).

$^1$H-NMR (CDCl$_3$) δ: 4.77 (2H, s), 7.05-7.19 (3H, m), 7.32-7.43 (1H, m), 7.52-7.63 (2H, m), 7.91 (1H, ddd, J=9.1, 7.6, 1.9 Hz), 8.35-8.41 (1H, m), 1H is not detected.

Reference Example 6

5-[(4-fluorophenyl)sulfonyl]-1-(2-fluoropyridin-3-yl)-1H-pyrazole-3-carbaldehyde

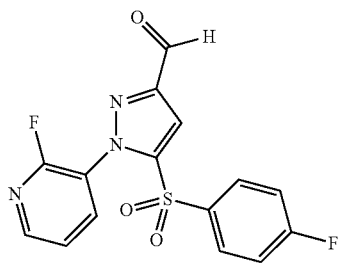 [SMILES: O=Cc1cc(S(=O)(=O)c2ccc(F)cc2)n(-c2cccnc2F)n1]

{5-[(4-Fluorophenyl)sulfonyl]-1-(2-fluoropyridin-3-yl)-1H-pyrazol-3-yl}methanol (135 mg) was dissolved in toluene (2 mL), manganese dioxide (167 mg) was added, and the mixture was stirred at 100° C. for 42 hr. The reaction mixture was allowed to cool to room temperature, and filtered through celite. The filtrate was concentrated under reduced pressure, and the residue was purified by silica gel column chromatography (eluent:hexane-ethyl acetate=19:1→3:1) to give the title compound as a colorless oil (yield 108 mg, yield 80%).

$^1$H-NMR (CDCl$_3$) δ: 7.11-7.21 (2H, m), 7.45 (1H, ddd, J=7.8, 4.9, 0.9 Hz), 7.53 (1H, s), 7.55-7.64 (2H, m), 7.98 (1H, ddd, J=9.1, 7.6, 1.9 Hz), 8.45 (1H, dt, J=4.9, 1.5 Hz), 10.00 (1H, s).

Reference Example 7 tert-butyl({5-[(4-fluorophenyl)sulfonyl]-1-(2-fluoropyridin-3-yl)-1H-pyrazol-3-yl}methyl)methylcarbamate

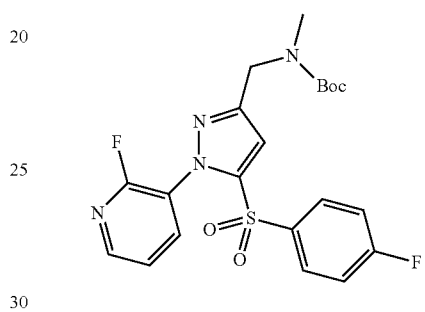

To a solution of 5-[(4-fluorophenyl)sulfonyl]-1-(2-fluoropyridin-3-yl)-1H-pyrazole-3-carbaldehyde (108 mg) in methanol (2 mL) were added methylammonium chloride (23 mg), anhydrous magnesium sulfate (56 mg) and triethylamine (34 mg). After stirring for 3 hr at room temperature, sodium borohydride (14 mg) was added under ice-cooling. The solvent was evaporated under reduced pressure, and to the residue were added water and ethyl acetate, and then di-tert-butyl bicarbonate (101 mg). The reaction Mixture was separated between the organic layer and the aqueous layer, and the separated aqueous layer was extracted again with ethyl acetate. The extract was washed with saturated brine, dried over anhydrous sodium sulfate, and concentrated under reduced pressure. The residue was purified by silica gel column chromatography (eluent:hexane-ethyl acetate=9:1→2:1) to give the title compound as a colorless oil (yield 132 mg, yield 93%).

$^1$H-NMR (CDCl$_3$) δ: 1.49 (9H, s), 2.89 (3H, brs), 4.45 (2H, brs), 7.03 (1H, brs), 7.08-7.18 (2H, m), 7.37 (1H, dd, J=7.4, 5.2 Hz), 7.50-7.63 (2H, m), 7.85-7.97 (1H, m), 8.31-8.40 (1H, m).

Reference Example 8 ethyl 1-(2-fluoropyridin-3-yl)-5-[(4-methoxyphenyl)sulfanyl]-1H-pyrazole-3-carboxylate

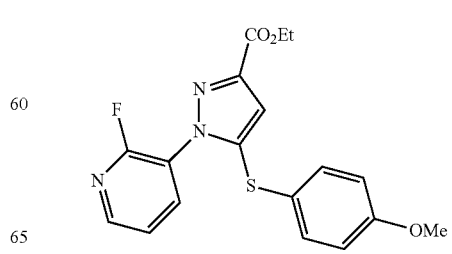

A solution of ethyl 1-(2-fluoropyridin-3-yl)-5-{[(trifluoromethyl)sulfonyl]oxy}-1H-pyrazole-3-carboxylate (351 mg), 4-methoxybenzenethiol (141 mg) and sodium carbonate (146 mg) in toluene (5 ml) was sufficiently deaerated, tris(dibenzylideneacetone)dipalladium(0) (17 mg) and 4,5-bis(diphenylphosphino)-9,9-dimethylxanthene (21 mg) were added, and the mixture was further deaerated. Under an argon atmosphere at 110° C., the mixture was stirred for 13 hr, and allowed to cool to room temperature. Ethyl acetate was added, and the mixture was filtered through a silica gel pad. The organic layer of the filtrate was washed with saturated brine, dried over anhydrous sodium sulfate, and concentrated under reduced pressure. The residue was purified by silica gel column chromatography (eluent:hexane-ethyl acetate=9:1→2:1) to give the title compound as a crude yellow oil.

Reference Example 9 ethyl 1-(2-fluoropyridin-3-yl)-5-[(4-methoxyphenyl)sulfanyl]-1H-pyrazole-3-carboxylate

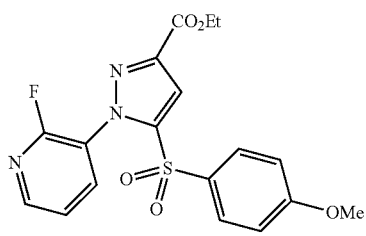 [SMILES: CCOC(=O)c1cc(S(=O)(=O)c2ccc(OC)cc2)n(-c2cccnc2F)n1]

According to the method of Reference Example 4 and using crude ethyl 1-(2-fluoropyridin-3-yl)-5-[(4-methoxyphenyl)sulfanyl]-1H-pyrazole-3-carboxylate instead of crude ethyl 5-[(4-fluorophenyl)sulfanyl]-1-(2-fluoropyridin-3-yl)-1H-pyrazole-3-carboxylate, the compound was synthesized (2 step yield 46%).

$^1$H-NMR (CDCl$_3$) δ: 1.41 (3H, t, J=6.9 Hz), 3.87 (3H, s), 4.44 (2H, q, J=7.3 Hz), 6.85-6.95 (2H, m), 7.38 (1H, dd, J=7.6, 4.8 Hz), 7.44-7.51 (2H, m), 7.53 (1H, s), 7.86-8.00 (1H, m), 8.39 (1H, d, J=5.0 Hz).

Reference Example 10

{1-(2-fluoropyridin-3-yl)-5-[(4-methoxyphenyl)sulfonyl]-1H-pyrazol-3-yl}methanol

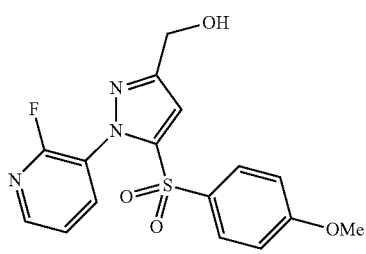 [SMILES: COc1ccc(S(=O)(=O)c2cc(CO)nn2-c2cccnc2F)cc1]

According to the method of Reference Example 5 and using ethyl 1-(2-fluoropyridin-3-yl)-5-[(4-methoxyphenyl)sulfonyl]-1H-pyrazole-3-carboxylate instead of ethyl 5-[(4-fluorophenyl)sulfonyl]-1-(2-fluoropyridin-3-yl)-1H-pyrazole-3-carboxylate, the compound was synthesized (yield 97%).

$^1$H-NMR (CDCl$_3$) δ: 1.97-2.05 (1H, m), 3.86 (3H, s), 4.76 (2H, d, J=5.8 Hz), 6.84-6.92 (2H, m), 7.08 (1H, s), 7.36 (1H, ddd, J=7.7, 5.0, 1.1 Hz), 7.43-7.50 (2H, m), 7.91 (1H, ddd, J=9.2, 7.6, 1.9 Hz), 8.35 (1H, dt, J=4.8, 1.4 Hz).

Reference Example 11

1-(2-fluoropyridin-3-yl)-5-[(4-methoxyphenyl)sulfonyl]-1H-pyrazole-3-carbaldehyde

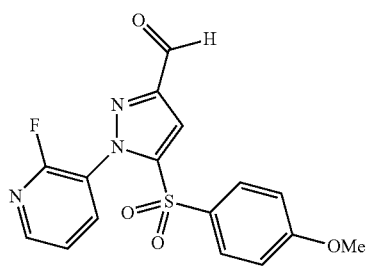 [SMILES: COc1ccc(S(=O)(=O)c2cc(C=O)nn2-c2cccnc2F)cc1]

According to the method of Reference Example 6 and using {1-(2-fluoropyridin-3-yl)-5-[(4-methoxyphenyl)sulfonyl]-1H-pyrazol-3-yl}methanol instead of {5-[(4-fluorophenyl)sulfonyl]-1-(2-fluoropyridin-3-yl)-1H-pyrazol-3-yl}methanol, the compound was synthesized (yield 91%).

$^1$H-NMR (CDCl$_3$) δ: 3.87 (3H, s), 6.86-6.95 (2H, m), 7.39-7.53 (4H, m), 7.94-8.05 (1H, m), 8.43 (1H, d, J=5.0 Hz), 9.99 (1H, s).

Reference Example 12 ethyl 1-(2-fluoropyridin-3-yl)-5-[(3-methylphenyl)sulfanyl]-1H-pyrazole-3-carboxylate

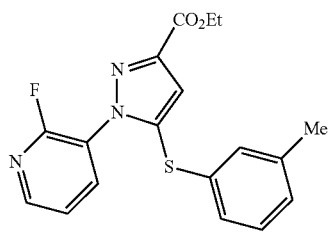 [SMILES: CCOC(=O)c1cc(Sc2cccc(C)c2)n(-c2cccnc2F)n1]

A solution of ethyl 1-(2-fluoropyridin-3-yl)-5-{[(trifluoromethyl)sulfonyl]oxy}-1H-pyrazole-3-carboxylate (575 mg), 3-methylbenzenethiol (224 mg) and sodium carbonate (238 mg) in toluene (7.5 mL) was sufficiently deaerated, tris(dibenzylideneacetone)dipalladium(0) (41 mg) and 4,5-bis(diphenylphosphino)-9,9-dimethylxanthene (52 mg) were added, and the mixture was further deaerated. Under an argon atmosphere at 130° C., the mixture was stirred for 28 hr and allowed to cool to room temperature. Ethyl acetate was added and the mixture was filtered through a basic silica gel pad. The filtrate was concentrated under reduced pressure, and the obtained residue was purified by silica gel column chromatography (eluent:hexane-ethyl acetate=9:1→2:1) to give the title compound as a crude yellow oil (yield 334 mg).

Reference Example 13 ethyl 1-(2-fluoropyridin-3-yl)-5-[(3-methylphenyl)sulfonyl]-1H-pyrazole-3-carboxylate

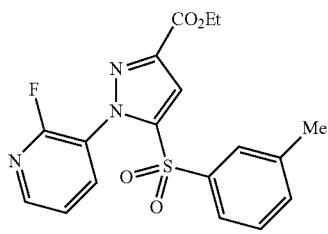 [SMILES: CCOC(=O)c1cc(S(=O)(=O)c2cccc(C)c2)n(-c2cccnc2F)n1]

To a solution of crude ethyl 1-(2-fluoropyridin-3-yl)-5-[(3-methylphenyl)sulfanyl]-1H-pyrazole-3-carboxylate (334 mg) in ethyl acetate (7.5 mL) was added 3-chloroperbenzoic acid (1.59 g). The mixture was stirred at room temperature for 3 hr, treated with saturated aqueous sodium thiosulfate solution, and extracted with ethyl acetate. The extract was washed with water, saturated aqueous sodium hydrogen carbonate solution and saturated brine, dried over anhydrous sodium sulfate, and concentrated under reduced pressure. The residue was purified by silica gel column chromatography (eluent: hexane-ethyl acetate=9:1→2:1) to give the title compound as a colorless oil (yield 384 mg, 2 steps yield 62%).
$^1$H-NMR (CDCl$_3$) δ: 1.41 (3H, t, J=7.2 Hz), 2.35 (3H, s), 4.44 (2H, q, J=6.9 Hz), 7.29 (1H, s), 7.32-7.41 (3H, m), 7.41-7.48 (1H, m), 7.60 (1H, s), 7.92 (1H, ddd, J=9.1, 7.6, 1.9 Hz), 8.39 (1H, dt, J=4.6, 1.5 Hz).

Reference Example 14

{1-(2-fluoropyridin-3-yl)-5-[(3-methylphenyl)sulfonyl]-1H-pyrazol-3-yl}methanol

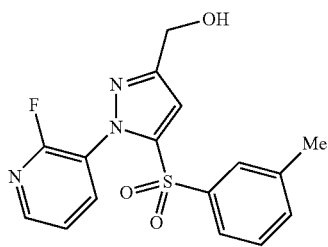 [SMILES: Cc1cccc(S(=O)(=O)c2cc(CO)nn2-c2cccnc2F)c1]

A solution of ethyl 1-(2-fluoropyridin-3-yl)-5-[(3-methylphenyl)sulfonyl]-1H-pyrazole-3-carboxylate (384 mg) in tetrahydrofuran (5 mL) was cooled to −78° C., a 1.5 mol/L solution (2.6 mL) of diisobutylaluminum hydride in toluene was added dropwise. The reaction mixture was stirred for 1 hr at 0° C., treated with 1 mol/L hydrochloric acid, and the mixture was extracted with ethyl acetate. The extract was washed with water, saturated aqueous sodium hydrogen carbonate solution and saturated brine, dried over anhydrous sodium sulfate, and concentrated under reduced pressure to give the title compound as a colorless oil (yield 320 mg, yield 94%)

$^1$H-NMR (CDCl$_3$) δ: 2.00 (1H, brs), 2.34 (3H, s), 4.77 (2H, d, J=4.2 Hz), 7.15 (1H, s), 7.28 (1H, s), 7.30-7.45 (4H, m), 7.91 (1H, ddd, J=9.2, 7.5, 1.9 Hz), 8.35 (1H, dt, J=4.9, 1.5 Hz).

Reference Example 15

1-(2-fluoropyridin-3-yl)-5-[(3-methylphenyl)sulfonyl]-1H-pyrazole-3-carbaldehyde

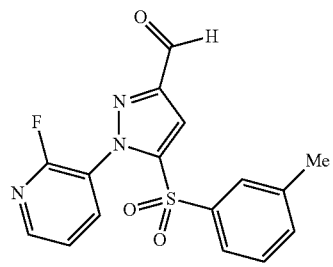 [SMILES: Cc1cccc(S(=O)(=O)c2cc(C=O)nn2-c2cccnc2F)c1]

{1-(2-Fluoropyridin-3-yl)-5-[(3-methylphenyl)sulfonyl]-1H-pyrazol-3-yl}methanol (320 mg) was dissolved in toluene (5 mL), manganese dioxide (802 mg) was added, and the mixture was stirred at 90° C. for 4 hr. The reaction mixture was allowed to cool to room temperature, and filtered through celite. The filtrate was concentrated under reduced pressure, and the residue was purified by silica gel column chromatography (eluent:hexane-ethyl acetate=9:1→2:1) to give the title compound as a colorless oil (yield 266 mg, yield 83%).
$^1$H-NMR (CDCl$_3$) δ: 2.35 (3H, s), 7.30 (1H, s), 7.32-7.39 (2H, m), 7.39-7.49 (2H, m), 7.53 (1H, s), 7.98 (1H, ddd, J=9.1, 7.6, 1.9 Hz), 8.43 (1H, dt, J=4.9, 1.5 Hz), 10.00 (1H, s).

Reference Example 16 tert-butyl({1-(2-fluoropyridin-3-yl)-5-[(3-methylphenyl)sulfonyl]-1H-pyrazol-3-yl}methyl)methylcarbamate

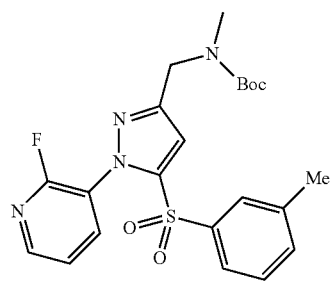 [SMILES: Cc1cccc(S(=O)(=O)c2cc(CN(C)C(=O)OC(C)(C)C)nn2-c2cccnc2F)c1]

To a solution of 1-(2-fluoropyridin-3-yl)-5-[(3-methylphenyl)sulfonyl]-1H-pyrazole-3-carbaldehyde (265 mg) in methanol (4 mL) were added methylammonium chloride (57 mg), anhydrous magnesium sulfate (139 mg) and triethylamine (85 mg). After stirring for 2 hr at room temperature, sodium borohydride (35 mg) was added under ice-cooling and the mixture was stirred at room temperature for 1 hr. The solvent was evaporated under reduced pressure. To the residue were added water and ethyl acetate, and then di-tert-butyl bicarbonate (251 mg). The reaction mixture was separated between the organic layer and the aqueous layer, and the separated aqueous layer was extracted again with ethyl acetate. The extract was washed with saturated brine, dried over anhydrous sodium sulfate, and concentrated under reduced pressure. The residue was purified by basic silica gel column chromatography (eluent:hexane-ethyl acetate=9:1→2:1) to give the title compound as a colorless oil (yield 302 mg, yield 85%).

$^1$H-NMR (CDCl$_3$) δ: 1.49 (9H, s), 2.34 (3H, s), 2.90 (3H, brs), 4.45 (2H, brs), 7.03 (1H, brs), 7.22-7.48 (5H, m), 7.85-7.97 (1H, m), 8.34 (1H, dt, J=3.3, 1.6 Hz).

Reference Example 17 ethyl 5-[(3-bromophenyl)sulfanyl]-1-(2-fluoropyridin-3-yl)-1H-pyrazole-3-carboxylate

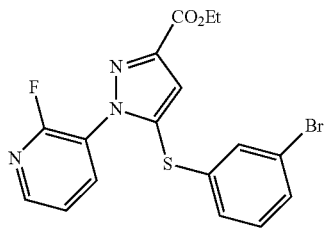 [SMILES: CCOC(=O)c1cc(Sc2cccc(Br)c2)n(-c2cccnc2F)n1]

A solution of ethyl 1-(2-fluoropyridin-3-yl)-5-{[(trifluoromethyl)sulfonyl]oxy}-1H-pyrazole-3-carboxylate (767 mg), 3-bromobenzenethiol (567 mg) and sodium carbonate (424 mg) in toluene (10 mL) was sufficiently deaerated, tris(dibenzylideneacetone)dipalladium(0) (92 mg) and 4,5-bis(diphenylphosphino)-9,9-dimethylxanthene (116 mg) were added, and the mixture was further deaerated. Under an argon atmosphere at 110° C., the reaction mixture was stirred for 16 hr, and allowed to cool to room temperature. Ethyl acetate was added and the mixture was filtered through a basic silica gel pad. The filtrate was concentrated under reduced pressure, and the residue was purified by silica gel column chromatography (eluent:hexane-ethyl acetate=9:1→2:1) to give the title compound as a crude yellow oil (yield 869 mg).

Reference Example 18 ethyl 5-[(3-bromophenyl)sulfonyl]-1-(2-fluoropyridin-3-yl)-1H-pyrazole-3-carboxylate

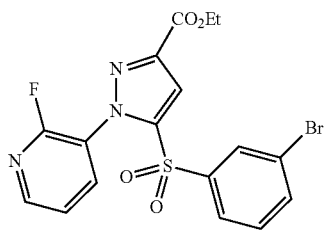 [SMILES: CCOC(=O)c1cc(S(=O)(=O)c2cccc(Br)c2)n(-c2cccnc2F)n1]

To a solution of crude ethyl 5-[(3-bromophenyl)sulfanyl]-1-(2-fluoropyridin-3-yl)-1H-pyrazole-3-carboxylate (869 mg) in ethyl acetate (10 mL) was added 3-chloroperbenzoic acid (2.73 g). The mixture was stirred at room temperature for 3 hr, treated with saturated aqueous sodium thiosulfate solution, and extracted with ethyl acetate. The extract was washed with water, saturated aqueous sodium hydrogen carbonate solution and saturated brine, dried over anhydrous sodium sulfate and concentrated under reduced pressure. The residue was purified by basic silica gel column chromatography (eluent:hexane-ethyl acetate=19:1→4:1) to give the title compound as a colorless oil (yield 410 mg, 2 steps yield 45%).

$^1$H-NMR (CDCl$_3$) δ: 1.41 (3H, t, J=7.2 Hz), 4.45 (2H, q, J=6.9 Hz), 7.31-7.46 (2H, m), 7.49-7.55 (1H, m), 7.60 (1H, t, J=1.7 Hz), 7.63 (1H, s), 7.77 (1H, dq, J=8.0, 1.0 Hz), 7.90 (1H, ddd, J=9.1, 7.6, 1.9 Hz), 8.43 (1H, dt, J=4.7, 1.6 Hz).

Reference Example 19

{5-[(3-bromophenyl)sulfonyl]-1-(2-fluoropyridin-3-yl)-1H-pyrazol-3-yl}methanol

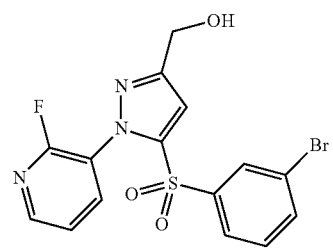 [SMILES: O=S(=O)(c1cccc(Br)c1)c1cc(CO)nn1-c1cccnc1F]

A solution of ethyl 5-[(3-bromophenyl)sulfonyl]-1-(2-fluoropyridin-3-yl)-1H-pyrazole-3-carboxylate (467 mg) in tetrahydrofuran (5 mL) was cooled to −78° C., and a 1.5 mol/L solution (2.7 mL) of diisobutylaluminum hydride in toluene was added dropwise. The reaction mixture was stirred at 0° C. for 2 hr, treated with 1 mol/L hydrochloric acid, and extracted with ethyl acetate. The extract was washed with water, saturated aqueous sodium hydrogen carbonate solution and saturated brine, dried over anhydrous sodium sulfate, and concentrated under reduced pressure to give the title compound as a yellow oil (yield 371 mg, yield 88%).

$^1$H-NMR (CDCl$_3$) δ: 2.19 (1H, brs), 4.77 (2H, brs), 7.19 (1H, s), 7.29-7.43 (2H, m), 7.50 (1H, dq, J=8.0, 1.0 Hz), 7.60 (1H, t, J=1.9 Hz), 7.69-7.79 (1H, m), 7.88 (1H, ddd, J=9.1, 7.6, 1.9 Hz), 8.39 (1H, dt, J=4.7, 1.6 Hz).

Reference Example 20

5-[(3-bromophenyl)sulfonyl]-1-(2-fluoropyridin-3-yl)-1H-pyrazole-3-carbaldehyde

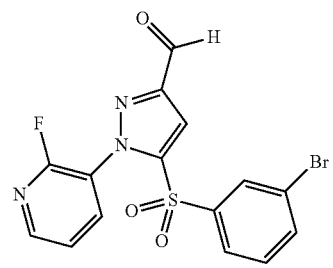

{5-[(3-Bromophenyl)sulfonyl]-1-(2-fluoropyridin-3-yl)-1H-pyrazol-3-yl}methanol (371 mg) was dissolved in toluene (5 mL), manganese dioxide (626 mg) was added and the mixture was stirred at 90° C. for 5 hr. The reaction mixture was allowed to cool to room temperature, and filtered through celite. The filtrate was concentrated under reduced pressure, and the residue was purified by silica gel column chromatography (eluent:hexane-ethyl acetate=19:1→3:1) to give the title compound as a colorless solid (yield 280 mg, yield 76%).

$^1$H-NMR (CDCl$_3$) δ: 7.32-7.42 (1H, m), 7.42-7.49 (1H, m), 7.53 (1H, dt, J=7.9, 1.3 Hz), 7.57-7.63 (2H, m), 7.78 (1H, dq, J=7.9, 1.0 Hz), 7.96 (1H, ddd, J=9.1, 7.6, 2.1 Hz), 8.47 (1H, dt, J=4.9, 1.5 Hz), 10.01 (1H, s).

Reference Example 21 tert-butyl({5-[(3-bromophenyl)sulfonyl]-1-(2-fluoropyridin-3-yl)-1H-pyrazol-3-yl}methyl)methylcarbamate

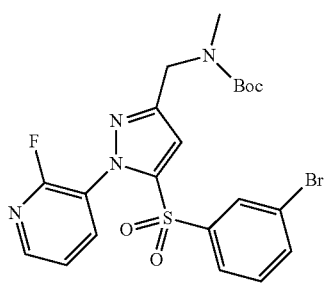 [SMILES: CN(Cc1cc(S(=O)(=O)c2cccc(Br)c2)n(-c2cccnc2F)n1)C(=O)OC(C)(C)C]

To a solution of 5-[(3-bromophenyl)sulfonyl]-1-(2-fluoropyridin-3-yl)-1H-pyrazole-3-carbaldehyde (270 mg) in methanol (3.5 mL) were added methylammonium chloride (49 mg), anhydrous magnesium sulfate (119 mg) and triethylamine (73 mg). After stirring for 3 hr at room temperature, sodium borohydride (37 mg) was added under ice-cooling, and the mixture was further stirred at room temperature for 1 hr. The solvent was evaporated under reduced pressure. To the residue were added water and ethyl acetate, and then di-tert-butyl bicarbonate (215 mg). The reaction mixture was separated into organic layer and aqueous layer, and the separated aqueous layer was extracted again with ethyl acetate. The extract was washed with saturated brine, dried over anhydrous sodium sulfate, and concentrated under reduced pressure. The residue was purified by silica gel column chromatography (eluent:hexane-ethyl acetate=9:1→2:1) to give the title compound as a colorless oil (yield 315 mg, yield 91%).

$^1$H-NMR (CDCl$_3$) δ: 1.49 (9H, s), 2.90 (3H, brs), 4.46 (2H, brs), 7.08 (1H, brs), 7.30-7.43 (2H, m), 7.50 (1H, d, J=8.0 Hz), 7.58 (1H, t, J=1.9 Hz), 7.74 (1H, dq, J=8.2, 0.8 Hz), 7.89 (1H, ddd, J=9.2, 7.5, 1.9 Hz), 8.38 (1H, dt, J=4.9, 1.5 Hz).

Reference Example 22 tert-butyl({5-[(3-cyanophenyl)sulfonyl]-1-(2-fluoropyridin-3-yl)-1H-pyrazol-3-yl}methyl)methylcarbamate

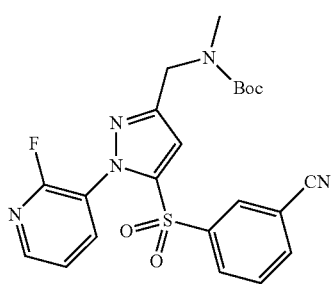 [SMILES: CN(Cc1cc(S(=O)(=O)c2cccc(C#N)c2)n(-c2cccnc2F)n1)C(=O)OC(C)(C)C]

A solution of tert-butyl({5-[(3-bromophenyl)sulfonyl]-1-(2-fluoropyridin-3-yl)-1H-pyrazol-3-yl}methyl)methylcarbamate (315 mg) and zinc cyanide (107 mg) in dimethylformamide (3 mL) was sufficiently deaerated, tetrakis(triphenylphosphine)palladium(0) (138 mg) was added, and the mixture was further deaerated. After stirring under an argon atmosphere at 110° C. for 2 hr, the reaction mixture was allowed to cool to room temperature, washed with water and saturated brine, dried over anhydrous sodium sulfate, and concentrated under reduced pressure. The residue was purified by silica gel column chromatography (eluent:hexane-ethyl acetate=9:1→2:1) to give the title compound as a yellow oil (yield 247 mg, yield 87%).

$^1$H-NMR (CDCl$_3$) δ: 1.50 (9H, s), 2.91 (3H, brs), 4.47 (2H, brs), 7.13 (1H, brs), 7.42 (1H, dd, J=7.9, 4.9 Hz), 7.57-7.67 (1H, m), 7.70-7.83 (2H, m), 7.85-8.00 (2H, m), 8.41 (1H, dt, J=4.9, 1.3 Hz).

Example 1

1-{5-[(4-fluorophenyl)sulfonyl]-1-(2-fluoropyridin-3-yl)-1H-pyrazol-3-yl}-N-methylmethanamine hydrochloride

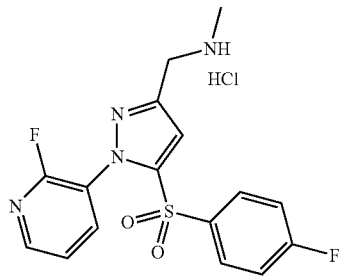 [SMILES: CNCc1cc(S(=O)(=O)c2ccc(F)cc2)n(-c2cccnc2F)n1 ; Cl]

tert-Butyl({5-[(4-fluorophenyl)sulfonyl]-1-(2-fluoropyridin-3-yl)-1H-pyrazol-3-yl}methyl)methylcarbamate (132 mg) was dissolved in ethyl acetate (2 ml) and 2-propanol (1 mL), and 4 mol/L hydrogen chloride-ethyl acetate solution (3 mL) was added. After stirring at room temperature for 2 hr, the reaction mixture was concentrated under reduced pressure, and the residue was recrystallized from a mixed solvent of ethanol and ethyl acetate to give the title compound as colorless crystals (yield 83 mg, yield 73%). melting point 211-214° C.

$^1$H-NMR (DMSO-d$_6$) δ: 2.59 (3H, s), 4.25 (2H, s), 7.41-7.51 (2H, m), 7.52 (1H, s), 7.56-7.70 (3H, m), 8.11 (1H, ddd, J=9.5, 7.8, 1.9 Hz), 8.51 (1H, dt, J=4.9, 1.5 Hz), 9.24 (2H, brs).

Example 2

1-{1-(2-fluoropyridin-3-yl)-5-[(4-methoxyphenyl)sulfonyl]-1H-pyrazol-3-yl}-N-methylmethanamine hydrochloride

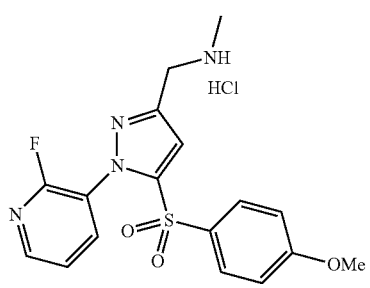 [SMILES: CNCc1cc(S(=O)(=O)c2ccc(OC)cc2)n(-c2cccnc2F)n1 ; Cl]

Using a method similar to that of Reference Example 7, 1-(2-fluoropyridin-3-yl)-5-[(4-methoxyphenyl)sulfonyl]-1H-pyrazole-3-carbaldehyde was subjected to reductive amination, and the compound was synthesized using 4 mol/L hydrogen chloride-ethyl acetate solution. melting point 222-225° C.

$^1$H-NMR (DMSO-$d_6$) δ: 2.58 (3H, s), 3.85 (3H, s), 4.23 (2H, s), 7.06-7.15 (2H, m), 7.41-7.52 (3H, m), 7.60 (1H, dd, J=7.7, 5.0 Hz), 8.07 (1H, ddd, J=9.6, 7.7, 1.9 Hz), 8.44-8.58 (1H, m), 9.27 (2H, brs).

Example 3

1-{1-(2-fluoropyridin-3-yl)-5-[(3-methylphenyl) sulfonyl]-1H-pyrazol-3-yl}-N-methylmethanamine hydrochloride

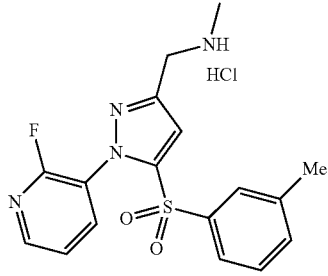 [SMILES: CNCc1cc(S(=O)(=O)c2cccc(C)c2)n(-c2cccnc2F)n1 ; Cl]

tert-Butyl({1-(2-fluoropyridin-3-yl)-5-[(3-methylphenyl) sulfonyl]-1H-pyrazol-3-yl}methyl)methylcarbamate (302 mg) was dissolved in ethyl acetate (2 mL) and 2-propanol (1 mL), and 4 mol/L hydrogen chloride-ethyl acetate solution (3 mL) was added. After stirring at room temperature for 2 hr, the reaction mixture was concentrated under reduced pressure. The residue was recrystallized from ethanol to give the title compound as colorless crystals (yield 216 mg, yield 83%). melting point 202-205° C.

$^1$H-NMR (DMSO-$d_6$) δ: 2.32 (3H, s), 2.59 (3H, s), 4.25 (2H, s), 7.25 (1H, s), 7.34-7.41 (1H, m), 7.46-7.53 (2H, m), 7.54-7.67 (2H, m), 8.09 (1H, ddd, J=9.5, 7.8, 1.9 Hz), 8.51 (1H, dt, J=4.9, 1.5 Hz), 9.24 (2H, brs).

Example 4

3-({1-(2-fluoropyridin-3-yl)-3-[(methylamino)methyl]-1H-pyrazol-5-yl}sulfonyl)benzonitrile hydrochloride

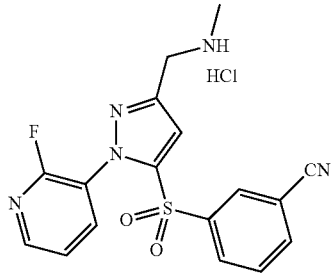 [SMILES: CNCc1cc(S(=O)(=O)c2cccc(C#N)c2)n(-c2cccnc2F)n1 ; Cl]

tert-Butyl({5-[(3-cyanophenyl)sulfonyl]-1-(2-fluoropyridin-3-yl)-1H-pyrazol-3-yl}methyl)methylcarbamate (247 mg) was dissolved in ethyl acetate (2 mL) and 2-propanol (1 mL), and 4 mol/L hydrogen chloride-ethyl acetate solution (3 mL) was added. After stirring at room temperature for 3 hr, the reaction mixture was concentrated under reduced pressure, and the residue was recrystallized from a mixed solvent of ethanol and water to give the title compound as colorless crystals (yield 184 mg, yield 86%). melting point 237-240° C.

$^1$H-NMR (DMSO-$d_6$) δ: 2.60 (3H, s), 4.26 (2H, s), 7.58-7.67 (2H, m), 7.79-7.88 (1H, m), 7.88-7.96 (1H, m), 8.04 (1H, t, J=1.7 Hz), 8.14 (1H, ddd, J=9.6, 7.7, 2.1 Hz), 8.28 (1H, dt, J=7.6, 1.3 Hz), 8.47-8.58 (1H, m), 9.25 (2H, brs).

Experimental Example 1

Proton Potassium-Adenosine Triphosphatase ($H^+$,$K^+$-ATPase) Inhibitory Activity Test According to the method of Wallmark et al. [Biochim. Biophys. Acta, 728, 31 (1983)], a microsomal fraction of gastric mucosa was prepared from the stomach of swine. First, the stomach was removed, washed with tap water, and immersed in 3 mol/L sodium chloride, and the surface of the mucosa was wiped with a paper towel. The gastric mucosa was removed, minced, and homogenized in a 0.25 mol/L sucrose solution (pH 6.8) containing 1 mmol/L EDTA and 10 mmol/L tris-hydrochloric acid using polytron (Kinematica). The obtained homogenate was centrifuged at 20,000×g for 30 min and the supernatant was centrifuged at 100,000×g for 90 min. The precipitate was suspended in 0.25 mol/L sucrose solution, the suspension was superimposed on a 0.25 mol/L sucrose solution containing 7.5% Ficoll, and centrifuged at 100,000×g for 5 hr. The fraction containing the interface between the both layers was recovered, and centrifugally washed with 0.25 mol/L sucrose solution.

The obtained microsomal fraction was used as proton, potassium-adenosine triphosphatase preparations.

To 50 mmol/L HEPES-Tris buffer (5 mmol/L magnesium chloride, 10 mmol/L potassium chloride, 10 μmol/L valinomycin, pH=6.5, 40 μL) containing 2.5 μg/mL enzyme preparation based on the protein concentration was added a test compound (5 μL) dissolved in 10% dimethyl sulfoxide solution, and the mixture was incubated at 37° C. for 30 min. A 2 mmol/L adenosine triphosphate tris salt solution (50 mmol/L HEPES-tris buffer (5 mmol/L magnesium chloride, pH 6.5), 5 μL) was added to start an enzyme reaction. The enzyme reaction was performed at 37° C. for 20 min, and then a malachite green solution (a mixture of 0.12% malachite green sulfate (2.5 mol/L) solution, 7.5% ammonium molybdate and 11% Tween 20 at a ratio of 100:25:2, 15 μL) was added to stop the reaction. The reaction mixture was stood at room temperature for 15 min, and the resulting reaction product of inorganic phosphorus and malachite green was measured by colorimetric quantification at a wavelength of 610 nm. In addition, the amount of inorganic phosphoric acid in a reaction solution free of potassium chloride was also measured in the same manner, and the value was extracted from that in the presence of potassium chloride, whereby the proton, potassium-adenosine triphosphatase activity was measured. The inhibitory rate (%) was determined from the activity value of the control and that at each concentration of the test compound, and 50% inhibitory concentration ($IC_{50}$) to proton, potassium-adenosine triphosphatase was determined. The results are shown in Table 1.

Experimental Example 2

The pKa value was calculated using the Physchem Batch (Ver. 10) of Advanced Chemistry Development, Inc. The results are shown in Table 1.

Experimental Example 3

ATP Content Test

Human hepatocellular liver carcinoma cell line HepG2 (ATCC No. HB-8065) was maintained and subcultured at 5% $CO_2$, 37° C. in a Dulbecco's modified Eagle medium (DMEM; Invitrogen) medium containing 10% fetal bovine serum (FBS; TRACE SCIENTIFIC LTD.), 1 mmol/L sodium pyruvate (Invitrogen), 2 mmol/L L-glutamine (Invitrogen), 50 IU/mL penicillin (Invitrogen), 50 μg/mL streptomycin (Invitrogen). Test reagent was prepared to 10 mM with DMSO, and diluted with DMEM medium containing 0.5% FBS, 1 mmol/L sodium pyruvate, 2 mmol/L L-glutamine, 50 IU/ml penicillin, 50 μg/mL streptomycin to the DMSO final concentration of 0.1%. HepG2 ($2\times10^4$ cells/well) was cultured on a 96 well white plate (Costar) together with the test reagent at 5% $CO_2$, 37° C. After culture for one day, the intracellular ATP content was measured with ATPLite™ (PerkinElmer Life Sciences). The results are shown in Table 1 as relative value (%) to the control (free of compound) at 100 μm ($n\geq3$, mean±SD).

Experimental Example 4

Caspase-3/7 Activity Test

The cells were cultured for one day according to a method similar to the method of Experimental Example 3, and the intracellular Caspase-3/7 activity was measured by Caspase-Glo 3/7 Assay (Promega). The results are shown in Table 1 as relative activity (%) of each test reagent when the maximum value of Caspase-3/7 activity on exposure to staurosporine as 100%, and activity without addition of test reagent as 0% ($n\geq3$, mean±SD).

Experimental Example 5

Histamine-Stimulated Acid Secretion Suppression Test Using Anesthetized Rat

7-Week-old Jcl: male SD rats were fasted for about 24 hr and used for the experiment. Under urethane (1.2 g/kg, i.p.) anesthesia, the abdomen was incised along the middle-spinal line and the pyloric ring was ligated. Test compound (1 mg/kg) was intravenously administered, the abdominal incision was sutured, and histamine dihydrochloride (30 mg/kg/10 mL) dissolved in physiological saline was subcutaneously administered. After 3 hr from histamine administration, the rats were killed with carbon dioxide gas. The stomach was isolated and the accumulated gastric fluid was collected. The gastric fluid amount was measured and the acid level was measured using acid titration apparatus COM-555 (HIRANUMA SANGYO Co., Ltd.), and the product thereof was taken as the acid secretion level. The acid secretion suppressive rate of the test compound was determined from the comparison with control. The results are shown in Table 1.

TABLE 1

| Ex. No. | $H^+/K^+$-ATPase inhibitory activity ($IC_{50}$, nM) | pKa value (calculated) | ATP content (%, 100 μM) | Caspase-3/7 activity (%, 100 μM) | acid secretion inhibitory rate (%, 1 mg/kg, intravenous administration, rat) |
|---|---|---|---|---|---|
| 1 | 120 | 7.46 | 95.9 | 0.1 | 98 |
| 2 | 350 | 7.52 | — | — | 82 |
| 3 | 88 | 7.50 | 90.1 | −0.2 | 95 |
| 4 | 230 | 7.40 | 98.5 | 1.0 | 99 |

From the results of Table 1, it is clear that compound (I) of the present invention has a superior $H^+/K^+$-ATPase inhibitory activity and lower pKa value, and shows extremely low cytotoxicity even at high concentrations. In addition, a strong acid secretion suppressive action was confirmed by intravenous administration to rats.

INDUSTRIAL APPLICABILITY

Compound (I) of the present invention shows a superior proton pump inhibitory effect. Conventional proton pump inhibitors such as omeprazole, lansoprazole and the like are converted to active forms in an acidic environment of stomach parietal cells and form a covalent bond with a cysteine residue of $H^+/K^+$-ATPase, and irreversibly inhibit the enzyme activity. In contrast, compound (I) inhibits proton pump ($H^+/K^+$-ATPase) activity in a reversible and $K^+$ competitive inhibitory manner, and consequently suppresses acid secretion. Therefore, it is sometimes called a potassium-competitive acid blocker (P-CAB), or an acid pump antagonist (APA). Compound (I) rapidly exhibits the action, shows the maximum efficacy from the initial administration, and shows less influence by genetic polymorphism (less variation among patients). Moreover, since it has substituents $R^2$ and $R^3$ at the m-position and p-position of phenyl group, respectively, it can further improve pharmacokinetics and can simultaneously impart a stronger pharmacological action and a lower cytotoxic action as compared to conventional compounds having a proton pump inhibitory action. Accordingly, the present invention can provide a clinically useful agent for the prophylaxis or treatment of peptic ulcer (e.g., gastric ulcer, duodenal ulcer, anastomotic ulcer, ulcer caused by non-steroidal anti-inflammatory drug, ulcer due to postoperative stress etc.), Zollinger-Ellison syndrome, gastritis, erosive esophagitis, reflux esophagitis, symptomatic gastroesophageal reflux disease (Symptomatic GERD), Barrett's esophagus, functional dyspepsia, gastric cancer, stomach MALT lymphoma or hyperacidity; or a suppressant of upper gastrointestinal hemorrhage due to peptic ulcer, acute stress ulcer, hemorrhagic gastritis or invasive stress; and the like. Since compound (I) shows low toxicity and is superior in water-solubility, in vivo kinetics and efficacy expression, it is useful as a pharmaceutical composition. Since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, onset of inhibitory action on gastric acid secretion is rapid, and symptoms such as pain and the like can be alleviated rapidly.

This application is based on patent application No. 2009-077078 filed in Japan, the contents of which are encompassed in full herein.

The invention claimed is:
1. A compound represented by the formula (I)

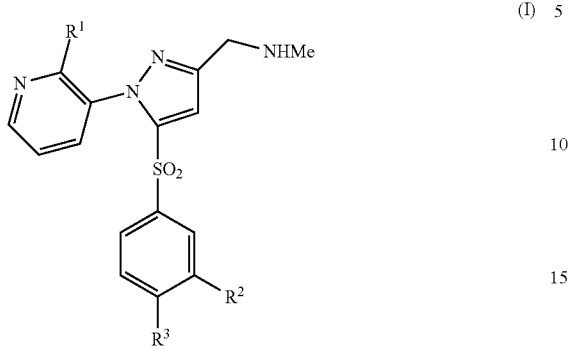

wherein R¹ is a fluorine atom, R² is a methyl group or a cyano group, and R³ is a hydrogen atom, or a salt thereof.

2. 1-{1-(2-Fluoropyridin-3-yl)-5-[(3-methylphenyl)sulfonyl]-1H-pyrazol-3-yl}-N-methylmethanamine or a salt thereof.

3. 3-({1-(2-Fluoropyridin-3-yl)-3-[(methylamino)methyl]-1H-pyrazol-5-yl}sulfonyl)benzonitrile or a salt thereof.

4. A pharmaceutical composition comprising the compound according to claim 1 or a salt thereof and a pharmaceutically acceptable carrier.

* * * * *